US007393996B2

(12) United States Patent
McCallum et al.

(10) Patent No.: US 7,393,996 B2

(45) Date of Patent: Jul. 1, 2008

(54) TOMATOES HAVING REDUCED POLYGALACTURONASE ACTIVITY CAUSED BY NON-TRANSGENIC MUTATIONS IN THE POLYGALACTURONASE GENE

(75) Inventors: Claire M. McCallum, Seattle, WA (US); Ann J. Slade, Kenmore, WA (US); Trenton G. Colbert, Seattle, WA (US); Vic C. Knauf, Bainbridge Island, WA (US); Susan Hurst, Seattle, WA (US)

(73) Assignee: Arcadia Biosciences Inc., Davis, CA (US)

( * ) Notice: Subject to any disclaimer, the term of this patent is extended or adjusted under 35 U.S.C. 154(b) by 0 days.

(21) Appl. No.: 11/246,793

(22) Filed: Oct. 7, 2005

(65) Prior Publication Data

US 2006/0037112 A1 Feb. 16, 2006

Related U.S. Application Data

(62) Division of application No. 10/691,374, filed on Oct. 22, 2003, now abandoned.

(60) Provisional application No. 60/420,228, filed on Oct. 22, 2002.

(51) Int. Cl.
*A01H 1/06* (2006.01)

(52) U.S. Cl. .................................... 800/276; 800/317.4

(58) Field of Classification Search ....................... None
See application file for complete search history.

(56) References Cited

U.S. PATENT DOCUMENTS

| | | | | |
|---|---|---|---|---|
| 4,801,540 | A | | 1/1989 | Hiatt et al. |
| 5,107,065 | A | | 4/1992 | Shewmaker et al. |
| 5,387,747 | A | | 2/1995 | Bru-Magniez et al. |
| 5,413,937 | A | | 5/1995 | Bridges et al. |
| 5,442,052 | A | | 8/1995 | Bird et al. |
| 5,447,867 | A | | 9/1995 | Bridges et al. |
| 5,453,566 | A | | 9/1995 | Shewmaker et al. |
| 5,569,831 | A | * | 10/1996 | DellaPenna ................. 800/286 |
| 5,759,829 | A | | 6/1998 | Shewmaker et al. |
| 5,994,075 | A | | 11/1999 | Goodfellow |

FOREIGN PATENT DOCUMENTS

| | | | |
|---|---|---|---|
| WO | WO-0063347 | | 10/2000 |
| WO | WO 01/75167 | * | 10/2001 |

OTHER PUBLICATIONS

Rose, R. E. *Lycopersiscon esculentum* gene for polygalacturonse (PG), exon 1. (1999) GenBank Accession X07410, pp. 1-2.*

Bird et al. The tomato polygalacturonase gene and ripening-specific expression in transgenic plants. (1993) GenBank Accession M37304.*

Brummell, et al., "Cell Wall Metabolism in Fruit Softening and Quality and Its Manipulation in Transgenic Plants", Plant Molecular Biology, vol. 47, p. 311-340, 2001.

Eriksson, et al., "Effect of the colorless Non-Ripening Mutation on Cell Wall Biochemistry and Gene Expression During Tomato Fruit Development and Ripening", Plant Physiology, vol. 136, pp. 4184-4197, Dec. 2004.

Grierson, et al., "Physiological and Genetic Factors Governing The Expression of the Polygalacturonase Gene in Ripening Tomatoes", the Molecular Basis of Plant Development, pp. 169-179, 1989.

Hobson, et al., "From Producer to Pantry—Using Biotechnology to Preserve Crop Quality", Aspects of Applied Biology, pp. 95-102, 1994.

Jarret, et al., "Ripening Behavior of the Green Ripe Tomato Mutant", J. Amer. Soc. Hort. Sci., vol. 109(5), pp. 712-717, 1984.

Knapp, et al., "Organization And Expression Of Polygalacturonase And Other Ripening Related Genes In Ailsa Cragi 'Neverripe' And 'Ripening Inhibitor' Tomato Mutants", Plant Molecular Biology, vol. 12, pp. 105-116, 1989.

Murray, et al, "Evaluation of Transgenic Tomato Fruit With Reduced Polygalacturonase Activity in combination with the rin Mutation", Postharvest Biology and Technology, pp. 91-101, 1995.

Schuch, et al., "Fruit Quality Characteristics of Transgenic Tomato Fruit With Altered Polygalacturonase Activity", HortScience, vol. 26(12), pp. 1517-1520, 1991.

Tucker, et al., "Changes in Polygalacturonase Isoenzymes During the 'Ripening' of Normal and Mutant Tomato Fruit", Eur. J. Biochem, vol. 112, pp. 119-124, 1980.

Zheng, et al., "Differential Expression of the Two Subunits of Tomato Polygalacturonase Isoenzyme 1 in Wild-Type and *rin* Tomato Fruit[1]", Plant Physiol, vol. 105, pp. 1189-1195, 1994.

Heinkoff, S. et al. (2003). "Single Nucleotide Mutations for Plant Functional Genomics," *Annual Review of Plant Biology* 54:375-401.

McCallum, C. M. et al. (Jul. 2003). "Tilling for Loss of Function Alleles in the Tomato Fruit Specific Polygalacturonase," American Society of Plant Biologists: Plant Biology 2003, Honolulu, Hawaii, 4 pages (Table of Contents).

Smith, C. J. S. et al. (Aug. 1988). "Antisens RNA Inhibition of Polygalacturonase Gene Expression in Transgenic Tomatoes," *Nature* 334:724-726.

Supplementary Partial European Search Report mailed Jun. 11, 2007, for European Application No. 03789950.7 filed Nov. 21, 2003, 4 pages.

Ali et al. (1982). "Purification and Characterization of the Polygalacturonases of Tomato Fruits," Aust. J. Plant Physiol., vol. 9, pp. 155-169.

Anthon et al. (2002). "Thermal Inactivation of Pectin Methylesterase, Polygalacturonase, and Peroxidase in Tomato Juice," Journal of Agricultural and Food Chemistry, vol. 50, pp. 6153-6159.

(Continued)

*Primary Examiner*—Stuart Baum
*Assistant Examiner*—Cathy Kingdon Worley
(74) *Attorney, Agent, or Firm*—Morrison & Foerster LLP

(57) ABSTRACT

A series of independent non-transgenic mutations found in the fruit PG gene of tomato; tomato plants having these mutations in their fruit PG gene; and a method of creating and identifying similar and/or additional mutations in the PG gene by screening pooled and/or individual tomato plants. The tomato plants of the present invention exhibit reduced PG enzyme activity and fruit that soften more slowly post harvest without having the inclusion of foreign nucleic acids in their genomes.

14 Claims, 9 Drawing Sheets

OTHER PUBLICATIONS

Atkinson et al. (1993). "A Polygalacturonase Gene From Kiwifruit (*Actinidia deliciosa*)," Plant Physiology 103: 669-670.

Bird et al. (1988). "The Tomato Polygalacturonase Gene and Ripening-Specific Expression in Transgenic Plants," Plant Mol. Biol., vol. 11, pp. 651-662.

Cantwell, M (Jan. 8, 2002). "Report to the California Tomato Commission: Tomato Variety Trials: Postharvest Evaluations for 2001."

Chen et al. (1999). "A Rapid DNA Minipreparation Method Suitable for AFLP and Other PCR Applications," Plant Molecular Biology Reporter, vol. 17, pp. 53-57.

Colbert et al. (Jun. 2001). "High-Throughput Screening for Induced Point Mutations," Plant Physiology, vol. 126, pp. 480-484.

Cooley et al. (1996). "Site-Selected Insertional Mutagenesis of Tomato With Maize AC and Ds Elements," Mol. Gen. Genet., vol. 252(1-2), pp. 184-194.

Della Penna et al. (1986). "Molecular Cloning of Tomato Fruit Polygalacturonase: Analysis of Polygalacturonase mRNA Levels During Ripening," Proc. Natl. Acad. Sci. U.S.A., vol. 83, pp. 6240-6424.

Edan, Y. (1997). "Color and Firmness Classification of Fresh Market Tomatoes," Journal of Food Science, vol. 62(4) pp. 793-796.

Errington, N. (1997). "Changes in the force relaxation and compression response of tomatoes during ripening: The Effect of Continual Testing and Polygalacturonase Activity," Postharvest Biology and Technology, vol. 11, pp. 141-147.

Fachin et al. (2002). "Thermal and High-Pressure Inactivation of Tomato Polygalacturonase: A Kinetic Study," Journal of Food Science, vol. 67, pp. 1610-1615.

Grierson, D. (Nov. 11, 1986). "cDNA Clone For Tomato Polygalacturonase," Nucleic Acids Res., vol. 14(21), pp. 8595-8603.

Guo et al. (2004). "Protein Tolerance to Random Amino Acid Change," PNAS 101:9205-9210.

Hamilton, A.J. (1995). "Sense And Antisense Inactivation Of Fruit Ripening Genes in Tomato," Current Topics in Microbiol Immunol, vol. 197, pp. 77-89.

Henikoff et al. (2000). "Increased Coverage of Protein Families With the Blocks Database Servers," Nucl. Acids Res. Vol. 28, pp. 228-230.

Henikoff et al. (1999). "Blocks+: A Non-Redundant Database Of Protein Alignment Blocks Derived From Multiple Compilations," Bioinformatics vol. 15(6), pp. 471-479.

Henikoff et al. (1995). "Automated Construction and Graphical Presentation Of Protein Blocks From Unaligned Sequences," Gene, ISSN 0378-1119 Amsterdam, Elsevier, vol. 163, pp. GC17-GC26.

Hill et al. (1998). "Functional Analysis of Conserveed Histidines in ADP-Glucose Pyrophosphorylase From *Escherichia coli*," Biochemical and Biophysical Research Communications 244:573-577.

Innis, M. A. et al. eds. (1990). PCR Protocols: A Guide to Methods and Applications. Academic Press Inc., pp. 3-21.

Ju R. et al. (1994). "Cloning Of Polygalacturonase (PG) Cdna And Inhibition Effects Of Its Antisense RNA On The Expression Of PG Gene In Transgenic Tomato Plants," Chin. J. Biotechnol., vol. 10(2), pp. 67-74.

Kalaitzis et al. (1997). "Three Different Polygalacturonases Are Expressed In Tomatoe Leaf And Flower Abscission, Each With Different Temporal Expression Pattern," Plant Physiology, vol. 113, pp. 1303-1308.

Kramer et al. (1992). "Postharvest Evaluation Of Transgenic Tomatoes With Reduced Levels Of Polygalacturonase: Processing, Firmness And Disease Resistance," Postharvest Biology and Technology, vol. 1, pp. 241-255.

Lazar et al. (1988). "Transforming Growth Factor: Mutation of Aspartic Acid 47 and Leucine 48 Results in Different Biological Activities," Molecular and Cellular Biology 8:1247-1252.

Lesage et al. (1996). "Measurement of Tomato Firmness by Using a NON-Destructive Mechanical Sensor," Postharvest Biology and Technology, vol. 8, pp. 45-55.

Li et al. (May 2002). "Integrated Platform For Detection of DNA Sequence Variants Using Capillary Array Electrophoresis," Electrophoresis, vol. 23(10), pp. 1499-1511.

McCallum et al. (Apr. 2000). "Targeted Screening for Induced Mutations," Nature Biotechnology, vol. 18, pp. 455-457.

McCallum et al. (Jun. 2000). "Targeting Induced Local Lesions IN Genomes (Tilling) For Plant Functional Genomics," Plant Physiology, vol. 123, pp. 439-442.

Neff et al. (1998). "dCAPS, a Simple Technique For The Genetic Analysis of Single Nucleotide Polymorphisms: Experimental Applications In Arabidopsis Thaliana Genetics," The Plant Journal, vol. 14, pp. 387-392.

Oleykowski et al. (1998). "Mutation Detection Using a Novel Plant Endonuclease," Nucleic Acids Research, vol. 14, pp. 4597-4602.

Pressey (1988). "Reevaluation Of The Changes In Polygalacturonases In Tomatoes During Ripening," Planta, vol. 174, pp. 39-43.

Sheehy et al. (1998). "Reduction of Polygalacturonase Activity in Tomato Fruit by Antisense RNA," PNAS, vol. 85, pp. 8805-8809.

Sitrit and Bennett (1998). "Regulation Of Tomato Fruit Polygalacturonase mRNA Accumlation By Ethylene: A Re-Examination," Plant Physiol, vol. 116, pp. 1145-1150.

Smith, C.J. et al. (1990). "Expression Of A Truncated Tomato Polygalacturonase Gene Inhibits Expression Of The Endogenous Gene In Transgenic Plants," Mol. Gen. Genet. vol. 224(3), pp. 477-481.

Stewart et al. (1993). "A Rapid CTAB DNA Isolation Technique Useful for RAPD Fingerprinting and Other PCR Applications," Bio Techniques, vol. 14(5), pp. 748-749.

Vrebalov et al. "A MADS-Box Gene Necessary for Fruit Ripening at the Tomato Ripening inhibitor (Rin) Locus," Science, vol. 296, pp. 343-346.

* cited by examiner

TOMATOES HAVING REDUCED POLYGALACTURONASE ACTIVITY CAUSED BY NON-TRANSGENIC MUTATIONS IN THE POLYGALACTURONASE GENE

PRIORITY

This is a divisional of U.S. patent application Ser. No. 10/691,374, filed Oct. 22, 2003 now abandoned, which was a non-provisional application of provisional of Patent Application Ser. No. 60/420,228, filed Oct. 22, 2002.

FIELD OF THE INVENTION

This invention concerns mutations in the fruit polygalacturonase (PG) gene of tomato. This invention further concerns tomato plants having mutations in their PG genes. This invention further concerns a method that utilizes non-transgenic means to create tomato plants having mutations in their PG genes.

BACKGROUND

United States consumers spend more than $4 billion each year on fresh market tomatoes. During the summer months, most of these fresh market tomatoes are grown on farms located throughout the United States and then sold locally. During the cooler months, when locally grown tomatoes are not available, most of these tomatoes are grown in the southern portions of the United States and in Mexico and then shipped by truck throughout the rest of the country. Unfortunately, when these southern grown tomatoes are allowed to fully ripen on the vine before shipping, they do not remain in marketable condition long enough for supermarkets to shelve them and for consumers to buy them.

To prevent the tomatoes from rotting before they reach consumers, farmers typically pick, pack, and ship the tomatoes while green. Before sale, the green tomatoes are gassed with ethylene to redden them. These unripened "gassed" tomatoes do not spoil quickly, but they have developed a reputation for poor flavor, especially compared to the summer "vine-ripened" tomatoes.

Due to consumer dissatisfaction with the unripened "gassed" tomatoes, research and breeding efforts have focused on developing tomatoes that exhibit a longer shelf-life when they are allowed to ripen fully on the vine. One approach to developing longer shelf-life tomatoes is to use traditional breeding techniques, i.e., crossing tomato plants with desired characteristics and selecting those progeny plants with fruits exhibiting longer shelf-lives. While traditional breeding techniques have been used to develop most of the tomato cultivars used by growers today, these methods are very time intensive. It can take years to breed a novel tomato variety that may exhibit only a modest increase in shelf-life.

Another approach to developing longer shelf-life tomatoes is to use genetic techniques to manipulate the biochemical and physiological changes associated with the ripening process in tomatoes. One biochemical change in ripening fruit is the depolymerization and solubilization of cell wall polyuronides by the ripening-induced cell wall degrading enzyme, polygalacturonase (PG). Tomato fruit PG (Della Penna et al., Proc. Natl. Acad. Sci. U.S.A. 1986 83:6420-6424; Bird et al., Plant Mol. Biol. 1988 11:651-662) belongs to a family of tomato PG genes. PG enzyme activity increases dramatically during the ripening of many fruits, including tomato, and is the primary enzymatic activity responsible for cell wall polyuronide degradation.

For example, in U.S. Pat. Nos. 5,107,065; 5,442,052; 5,453,566; 5,569,831; and 5,759,829, tomato plants were transformed with DNA constructs encoding an antisense oligonucleotide for the PG gene. When expressed, the foreign DNA provided an RNA sequence capable of binding to the naturally existing mRNAs of the PG gene in the transformed tomato plant thereby preventing the translation of the mRNA into the PG protein. The fruit of transformed tomato plants showed improved properties in terms of slower softening post harvest, thereby increasing the shelf-life of the tomato.

Another research group, using a complicated series of transgenic manipulations involving transposon sequences from another plant species, created a "knock out" of the PG gene in tomato. Enzymatic analysis of fruit from plants containing the knock out of the PG gene showed at least a 1000-fold reduction in PG levels. See Cooley, M. B. and Yoder, J. I., *Plant Mol. Biol.,* 1998 Nov. 1, 38(4):521-30; Cooley et al., *Mol. Gen. Genet.* 1996 Aug. 27, 252(1-2):184-194.

This anti-sense and "knock-out" work indicates that fruit PG gene expression is not necessary for viable, normal tomato fruit production. While several features of the ripening process remain normal, transgenic tomatoes having reduced PG gene expression exhibit slower softening post harvest and increased shelf life. Additionally, these transgenic tomatoes exhibit a lower incidence of post-harvest disease infection due to the preservation of intact fruit skin and coat caused by the delayed softening. Therefore, the tomatoes with reduced PG have fewer cosmetic blemishes which deter customers.

Reduced PG enzyme activity is important not only to the fresh market tomato industry but also to the processed tomato industry. During commercial processing of tomatoes, pectin integrity of the tomato is lost by enzymatic degradation of the pectin by PG. In order to avoid this degradation, a rapid, high heat treatment is used to destroy the PG enzyme activity. The annual cost associated with the total energy required to bring millions of tons of tomatoes to a temperature sufficient to rapidly inactivate the PG enzyme is a significant cost to the tomato processing industries.

While the use of these genetic techniques has resulted in producing tomatoes with reduced PG gene expression, the genetic techniques used to date employ recombinant DNA being introduced into tomatoes. Since many consumers have clear preferences against genetically modified foods, it would be useful to have a tomato exhibiting reduced levels of fruit PG that was not the result of genetic engineering methods. However, to date, no one has ever found or described a naturally occurring "knockout" of the endogenous tomato PG gene. Therefore, a tomato with its fruit PG gene either knocked out or otherwise hindered would have tremendous value to the entire tomato industry.

SUMMARY OF THE INVENTION

In one aspect, this invention includes a tomato plant, tomato fruits, seeds, plant parts, and progeny thereof having reduced fruit polygalacturonase enzyme activity compared to the wild type tomato plants wherein the reduced fruit polygalacturonase enzyme activity is caused by non-transgenic mutation in the tomato fruit polygalacturonase gene.

In another aspect, this invention includes a tomato plant having tomato fruits which soften slower post harvest compared to wild type tomato fruits due to an altered polygalacturonase enzyme, as well as fruit, seeds, pollen, plant parts and progeny of that plant.

In another aspect, this invention includes food and food products incorporating tomato fruit having reduced polygalacturonase enzyme activity caused by a non-transgenic mutation in the fruit polygalacturonase gene.

In another aspect, this invention includes a tomato plant having reduced fruit polygalacturonase enzyme activity compared to the wild type tomato plants created by the steps of obtaining plant material from a parent tomato plant, inducing at least one mutation in at least one copy of a fruit polygalacturonase gene of the plant material by treating the plant material with a mutagen to create mutagenized plant material, culturing the mutagenized plant material to produce progeny tomato plants, analyzing progeny tomato plants to detect at least one mutation in at least one copy of a fruit polygalacturonase gene, selecting progeny tomato plants that have reduced fruit polygalacturonase enzyme activity compared to the parent tomato plant; and repeating the cycle of culturing the progeny tomato plants to produce additional progeny plants having reduced fruit polygalacturonase enzyme activity.

BRIEF DESCRIPTION OF THE SEQUENCE LISTING

SEQ. ID. NO.: 1 shows the DNA sequence between the start and stop codons for the coding region of Polygalacturonase (Gen Bank Accession NO. M37304).

SEQ. ID. NO.: 2 shows the protein sequence encoded by SEQ. ID. NO.: 1.

SEQ. ID. NOS.: 3-46 show the DNA sequences for Polygalacturonase specific primers of the present invention.

SEQ. ID. NO.: 47 shows the DNA sequence of the Polygalacturonase gene for Mutation 13345.

SEQ. ID. NO.: 48 shows the protein sequence encoded by SEQ. ID. NO.: 47.

SEQ. ID. NO.: 49 shows the DNA sequence of the Polygalacturonase gene for Mutation 13342.

SEQ. ID. NO.: 50 shows the protein sequence encoded by SEQ. ID. NO.: 49.

DETAILED DESCRIPTION

The present invention describes: a series of independent non-transgenic mutations created in the polygalacturonase (PG) gene of tomato; tomato plants having these mutations in their PG gene; and a method of creating and identifying similar and/or additional mutations in the PG gene of tomato plants. The present invention further describes tomato plants exhibiting reduced PG enzyme activity and slower fruit softening post harvest without the inclusion of foreign nucleic acids in the tomato plants' genomes.

Figure 1:
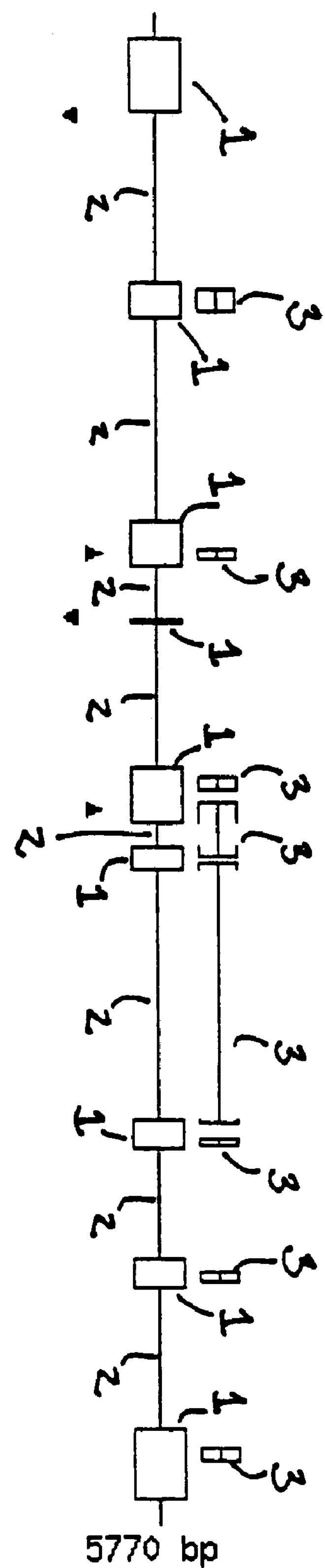
FIG. 1 is an illustration of the regions of the PG gene.

As shown in FIG. 1, the tomato fruit PG gene (GenBank accession no. M37304) consists of nine exons 1 separated by eight introns 2, and 5' and 3' untranslated regions. The DNA surrounding the gene regulates expression of the PG gene. The PG protein sequence contains eight highly conserved regions called blocks 3 (available at blocks.fhcrc.org/blocks-bin/getblock. sh?IPB000743), listed under IPB000773 at the Fred Hutchinson Cancer Research Center Blocks website. These regions are conserved amongst polygalacturonases from many organisms. Of all the conserved amino acid residues in the blocks, 15 amino acids are either invariant or are found in the majority of all polygalacturonases (using the criteria of only one other amino acid found at that position in a minority of protein sequences). J. G. Henikoff, et al., Nucl. Acids Res. 28:228-230 (2000). S. Henikoff, et al., Bioinformatics 15(6):471-479 (1999).

In order to create and identify the PG gene mutations and slower softening tomatoes of the present invention, a method known as TILLING was utilized. See McCallum, et al., *Nature Biotechnology* (April 2000), 18: 455-457; McCallum, et al., (June 2000) *Plant Physiology, Vol*. 123, pp. 439-442; and U.S. Pat. No. 5,994,075, all of which are incorporated herein by reference. In the basic TILLING methodology, plant material, such as seeds, are subjected to chemical mutagenesis, which creates a series of mutations within the genomes of the seeds' cells. The mutagenized seeds are grown into adult M1 plants and self-pollinated. DNA samples from the resulting M2 plants are pooled and are then screened for mutations in a gene of interest. Once a mutation is identified in a gene of interest, the seeds of the M2 plant carrying that mutation are grown into adult M3 plants and screened for the phenotypic characteristics associated with the gene of interest.

Any cultivar of tomato having at least one PG gene with substantial homology to Seq. I.D. No. 1 may be used in the present invention. The homology between the PG gene and Seq. I.D. No. 1 may be as low as 60% provided that the homology in the conserved regions of the gene are higher. Thus one of skill in the art may prefer a tomato cultivar having commercial popularity or one having specific desired characteristics in which to create their PG-mutated tomato plants. Alternatively, one of skill in the art may prefer a tomato cultivar having few polymorphisms, such as an in-bred cultivar, in order to facilitate screening for mutations within the PG gene.

In one embodiment of the present invention, seeds from the tomato plant are mutagenized and then grown into M1 plants. The M1 plants are then allowed to self-pollinate and seeds from the M1 plant are grown into M2 plants, which are then screened for mutations in their PG genes. However, one of skill in the art would understand that a variety of tomato plant materials, including but not limited to, seeds, pollen, plant tissue or plant cells, may be mutagenized in order to create the PG-mutated tomato plants of the present invention. However, the type of plant material mutagenized may affect when the plant DNA is screened for mutations. For example, when pollen is subjected to mutagenesis prior to pollination of a non-mutagenized plant, the seeds resulting from that pollination are grown into M1 plants. Every cell of the M1 plants will contain mutations created in the pollen, thus these M1 plants may then be screened for PG gene mutations instead of waiting until the M2 generation.

Mutagens creating primarily point mutations and short deletions, insertions, transversions, and or transitions (about 1 to about 5 nucleotides), such as chemical mutagens or radiation, may be used to create the mutations of the present invention. For example, but not limited to, mutagens such as ethyl methanesulfonate (EMS), methylmethane sulfonate (MMS), N-ethyl-N-nitrosurea (ENU), triethylmelamine (TEM), N-methyl-N-nitrosourea (MNU), procarbazine, chlorambucil, cyclophosphamide, diethyl sulfate, acrylamide monomer, melphalan, nitrogen mustard, vincristine, dimethylnitosamine, N-methyl-N'-nitro-Nitrosoguanidine (MNNG), nitrosoguanidine, 2-aminopurine, 7,12 dimethyl-benz(a)anthracene (DMBA), ethylene oxide, hexamethylphosphoramide, bisulfan, diepoxyalkanes (diepoxyoctane (DEO), diepoxybutane (BEB), and the like), 2-methoxy-6-chloro-9[3-(ethyl-2-chloro-ethyl)aminopropylamino] acridine dihydrochloride (ICR-170), formaldehyde, and the like may be used to mutagenize the plant tissue in order to create the PG gene mutations of the present invention. Spontaneous mutations in the fruit PG gene that may not have been directly caused by the mutagen can also be identified using the present invention.

Any method of plant DNA preparation known to those of skill in the art may be used to prepare the tomato plant DNA for PG mutation screening. For example, See D. H. Chen and Ronald, P. C., *Plant Molecular Biology Reporter* 17: 53-57 (1999); C. N. Stewart and Via, L E, *Bio Techniques*, 1993, Vol. 14(5): 748-749. Additionally, several commercial kits are available, including kits from Qiagen (Valencia, Calif.) and Qbiogene (Carlsbad, Calif.).

The prepared DNA from individual tomato plants are then pooled in order to expedite screening for mutations in the PG genes of the entire population of plants originating from the mutagenized plant tissue. The size of the pooled group is dependent upon the sensitivity of the screening method used. Preferably, groups of four or more individuals are pooled.

After the DNA samples are pooled, the pools are subjected to PG gene-specific amplification techniques, such as Polymerase Chain Reaction (PCR). For a general overview of PCR, see PCR Protocols: A Guide to Methods and Applications (Inns, M., Gelfand, D., Sninsky, J., and White, T., eds.), Academic Press, San Diego (1990). Any primer specific to the PG gene or the sequences immediately adjacent to the PG gene may be utilized to amplify the PG genes within the pooled DNA sample. Preferably, the primer is designed to amplify the regions of the PG gene where useful mutations are most likely to arise. For example, the primer should maximize the amount of exonic sequence of the PG gene and, likewise, avoid intronic sequences of the gene. Additionally, it is preferable for the primer to avoid known polymorphism sites in order to ease screening for point mutations. Furthermore, when specifically screening for mutations that will knock out the PG enzymatic activity, it is preferable to target the 5'-end of the PG gene or to target areas of the PG gene that are highly conserved. To facilitate detection of PCR products on a gel, the PCR primer may be labeled using any conventional labeling method. Exemplary primers (SEQ. ID. Nos.3-46) that have proven useful in identifying useful mutations within the PG gene sequence are shown below in Table 1.

TABLE 1

| NAME | SEQUENCE | SEQUENCE I.D. NO. |
|---|---|---|
| Lc_PG-L1 | TTGAGACGGGAGAAGACAAGCCAGA | 003 |
| Lc_PG-L2 | CCAACCATATGAACAACCTCACACATGC | 004 |
| Lc_PG-L3 | TGTGGGGTAGATCGATCCAGAGGTTG | 005 |
| Lc_PG-L4 | ACGCCTCGTACATTCGAGATCGTTG | 006 |
| Lc_PG-L5 | TCACAAGAAAAGGGATAGTTCAAAGTG | 007 |
| Lc_PG-L6 | TGAAGTCATTTCAAAACGAATCAAAT | 008 |
| LePG-L10-700 | TTCTCCTTCTCATTATTATTTTTGCTTCA TCA | 009 |
| LePG-L11-700 | CTGGAATTGCAAAAATTTGAAAGTGAATA A | 010 |
| PG1Lnew-IRD | TTGAGACGGGAGAAGACAAGCCAGAC | 011 |
| PG3Lnew-IRD | AGTGGCTTTCGTACTACATAATCTTAG | 012 |
| PG-5Lnew | CATGCAATAATTATTGACGAAATGTGGT | 013 |
| PG-L1 | TTGAGACGGGAGAAGACAAGCCAGA | 014 |
| PGL1 IRD700 | TGAGACGGGAGAAGACAAGCCAGAC | 015 |
| PG-L10 | TTCTCCTTCTCATTATTATTTTTGCTTCA TCA | 016 |
| PG-L11 | CTGGAATTGCAAAAATTTGAAAGTGAATA A | 017 |
| PGL12 | TTGACGAAATGTGGTTTTGGTACCTATAA TCTT | 018 |
| PGL14 | CACAAACGAATACATGCAGATTCTCAAAC A | 019 |
| PG-L2-700 | CCAACCATATGAACAACCTCACACATGC | 020 |
| PG-L2B | ATCTTCAATCTACCATATTGAAATATTG | 021 |
| PG-L2C | TACATTTGGTAGTGTTTCTTATCGTG | 022 |
| PG-L3-new | AGTGGCTTTCGTACTACATAATCTTAG | 023 |
| PG-L7 | CAAAAGACGAAATGATGAATAATTTTGCG AAT | 024 |
| PG-L8 | CACAAACGAATACATGCAGATTCTCAAAC A | 025 |
| PG-L8B | AGTAGAGTATATCCTTAAAAGAGAGC | 026 |
| PG-L9 | ACGCCTCTGACATTCGAGATCGTTG | 027 |
| Lc_PG-R1 | CCATGGAAAATAGCTTTTCCTCGCTTA | 028 |
| Lc_PG-R2 | CATTTTGATAATTCCTCACTAATCCGCTA A | 029 |
| Lc_PG-R3 | CAAGGGGTAATAGGTCCTGCCCAAA | 030 |
| Lc_PG-R4 | CTGCTTTTATTCGCCCATCCAAACG | 031 |
| Lc_PG-R5 | GAATCTCAAAGTTTTAATGATGTAAGGTG A | 032 |
| Lc_PG-R6 | TTATACAAAAGAGCTTCATCCTCTGAAAT | 033 |
| PG-R10 | CCTGTTGTATACATGGTTCAACTCGATCA CA | 034 |
| PG-R11 | CCTCTGAAATTTCTAGTGAAGTGCAGTGT GG | 035 |
| PG-R12 | TCCATGGAAAATGACTTTCCTCGCTTAC | 036 |
| PG-R13 | ATAGAAGATCTGCATGGACCTGAAAAGGT GA | 037 |
| PG-R14 | AAGTAATATTTGTGGCCTGCACATTTTGA G | 038 |
| PG-R15 | CCTAATTATTGTGCTAAGTCATTAACCAT AAAGAC | 039 |
| PGR16 | GACCATAGTCCAAAAGATCCATAAATTAG AAGAAAA | 040 |
| PGR17 | TGACATTATAGTTCAACAAGAAATACCAA AGGGATA | 041 |
| PG-R7 | ACCATGGAAAATAGCTTTCCTCGCTTAA | 042 |
| PG-R8 | CAAAGGGGTAATAGTCCTGCCCAAA | 043 |
| PG-R9 | CTACTTTTATTACGCCCATCCAAACG | 044 |
| PGseqint7 | AAGTGTAAATGTGTTGCTTTGTTTAGAAG TTTGG | 045 |
| Pgint8 | TGAAAAGAATCTCAAAGTTTTAATGATGT AAGGTGA | 046 |

The PCR amplification products may be screened for PG mutations using any method that identifies heteroduplexes between wild type and mutant genes. For example, but not limited to, denaturing high pressure liquid chromotography (dHPLC), constant denaturant capillary electrophoresis (CDCE), temperature gradient capillary electrophoresis (TGCE) (Q. Li, et al., *Electrophoresis*, 23(10):1499-1511 (May 2002), or by fragmentation using chemical cleavage, such as used in the high throughput method described by Colbert et al., *Plant Physiology*, 126:480-484 (June 2001).

Preferably the PCR amplification products are incubated with an endonuclease that preferentially cleaves mismatches in heteroduplexes between wild type and mutant sequences. Cleavage products are electrophoresed using an automated sequencing gel apparatus, and gel images are analyzed with the aid of a standard commercial image-processing program.

Mutations that reduce PG enzyme activity in the plant are desirable. Preferred mutations include those that prematurely truncate the translation of the PG protein, such as those mutations that create a stop codon within the amino acid sequence of the PG protein. Additional preferred mutations include those that cause the mRNA to be alternatively spliced, such as mutations in and around the intron splice sites within the mRNA. Furthermore, any mutations that create an amino acid change within one of the fifteen highly conserved residues of the PG polypeptide are also preferred.

Once an M2 plant having a mutated PG gene is identified, then the mutations are analyzed to determine its potential affect on the expression, translation, and/or activity of the PG enzyme. First, the PCR fragment containing the mutation is sequenced, using standard sequencing techniques, in order to determine the exact location of the mutation in relation to the overall PG gene sequence. Second, in order to determine the severity of the change, a LOGO analysis is performed on the amino acid sequence BLOCK in which a mutation is located. Protein BLOCKS are multiply-aligned, ungapped segments corresponding to the most highly conserved regions of the protein families. Henikoff et al., *Gene* 163: GC17-GC26 (1995). LOGOs are a graphical representation of aligned sequences where the size of each amino acid residue is proportional to its frequency in that position. The LOGO for a BLOCK is calculated from the position-specific scoring matrix (PSSM). Tomato PG belongs to the glycoside hydrolase protein family 28 (BLOCK IPB000743). One hundred and forty-seven members of this family were used to identify the seven conserved blocks within the family that are included in the BLOCKS database.

If the initial assessment of the mutation in the M2 plant appears to be in a useful position within the PG gene, then further phenotypic analysis of the tomato plant containing that mutation is pursued. First, the M2 plant is backcrossed twice in order to eliminate background mutations. Then the M2 plant is self-pollinated in order to create a plant that is homozygous for the PG mutation.

Physical and biochemical characteristics of these homozygous PG mutant plants are then assessed. Mutant PG tomatoes are evaluated for delayed softening compared to the normal (wild type) parental tomato lines. Normal fruit ripens such that the color of the tomato changes from light green to red. As this change happens, the fruit tends to become softer such that compression under a specified weight becomes greater and/or the force required to depress the surface of the fruit a specified distance becomes greater. See Cantwell, M. Report to the California Tomato Commission: Tomato Variety Trials: Postharvest Evaluations for 2001; Edan, Y., H. Pasternak, I. Shmulevich, D. Rachmani, D. Guedalia, S. Grinberg and E. Fallik. 1997. Color and firmness classification of fresh market tomatoes. J. Food Science 62(4): 793-796; Errington, N., J. R. Mitchell and G. A. Tucker. 1997. Changes in the force relaxation and compression responses of tomatoes during ripening: the effect of continual testing and polygalacturonase activity. Postharvest Biol. Tech. 11: 141-147; Lesage, P. and M-F. Destain. 1996. Measurement of tomato firmness by using a non-destructive mechanical sensor. Postharvest Biol. Tech. 8: 45-55.

Figure 2:
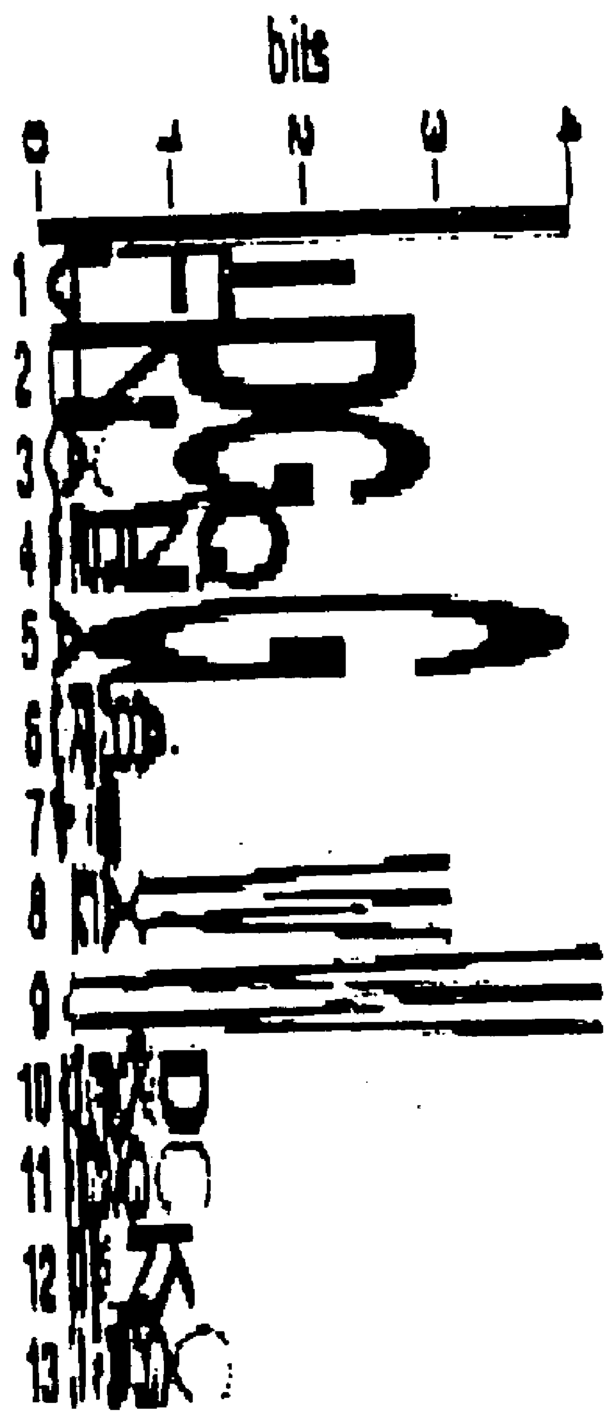
FIG. 2 is a LOGO analysis of Mutation 13345.

The following mutations are exemplary of the tomato mutations created and identified according to the present invention. One exemplary mutation, correlates with a change of G to A at nucleotide 1969 of SEQ. ID. NO. 1, counting A in the ATG of the START CODON as nucleotide position 1. This mutation results in a change from glycine to arginine at amino acid 178 in the expressed protein. The change from glycine to arginine at 178 is a dramatic amino acid change both in terms of charge and size. The G178R mutation is within block B of this family. As shown in FIG. 2, G178 is one of the fifteen most conserved residues within the glycoside hydrolase protein family. *Lycopersicon esculentum* seeds of the cultivar Shady Lady containing this mutation were deposited with the American Type Culture Collection, 10801 University Blvd., Mannassas, Va. 20110-2209, on Sep. 9, 2002 and given Accession No. 13345 and Patent Deposit Designation PTA-4702.

Figure 3:
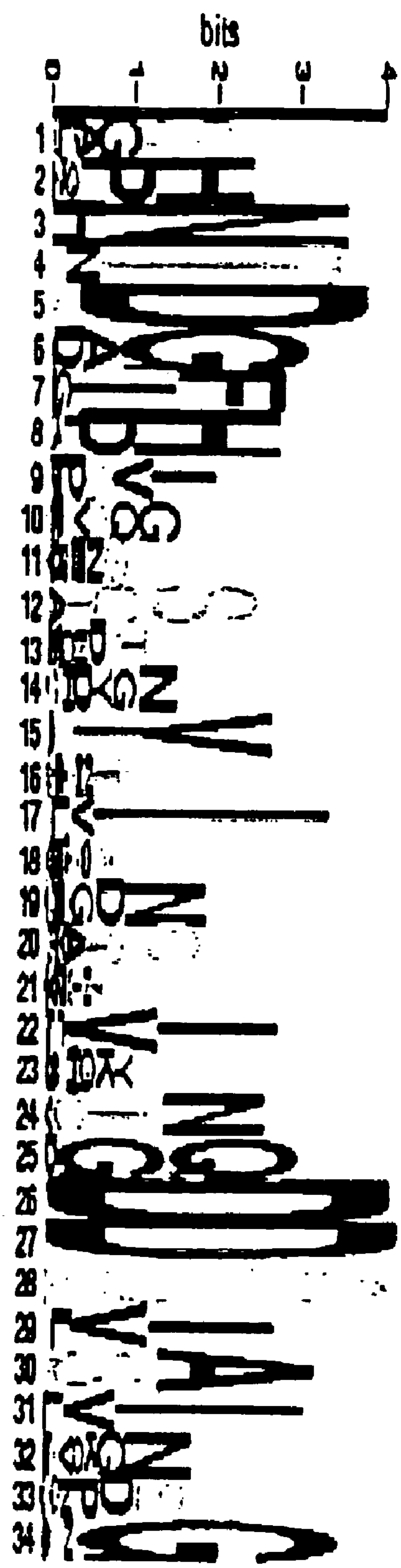
FIG. 3 is a LOGO analysis of Mutation 13342.

Another exemplary mutation, created and identified according to the present invention, correlates with a T to A change at nucleotide position 2940 of SEQ. ID. NO. 1, counting A in the ATG of the START CODON as nucleotide position 1. This mutation results in a change from histidine to glutamine at amino acid 252. The H252Q mutation is within block D of the glycoside hydrolase protein family. As shown in FIG. 3, H252Q is also a change in a very conserved region of this protein family. *Lycopersicon esculentum* seeds of the cultivar Shady Lady containing this mutation were deposited with the American Type Culture Collection, 10801 University Blvd., Mannassas, Va. 20110-2209, on Sep. 20, 2002 and given Accession No. 13342 and Patent Deposit Designation PTA-4702.

The following Examples are offered by way of illustration, not limitation.

EXAMPLE 1

Mutagenesis

In one embodiment of the present invention tomato seeds of cultivars Shady Lady (hybrid) and NC 84173 (inbred line provided by R. Gardner at the University of North Carolina) were vacuum infiltrated in $H_2O$ (ca. 4 min. with ca. 1000 seeds/100 ml $H_2O$). The seeds were then placed on a shaker (45 rpm) in a fume hood at ambient temperature. The mutagen ethyl methanesulfonate (EMS) was added to the imbibing seeds for final concentrations ranging from about 0.1% to about 1.6% (v/v). EMS concentrations of about 0.4 to about 1.2% were determined to be optimal for these studies. Following a 24-hour incubation, the EMS solution was replaced with fresh $H_2O$ (4× to an est. EMS dilution 1/2,000,000,000). The seeds were then rinsed under running water for ca. 1 hour. Finally, the mutagenized seeds were planted (96/tray) in potting soil and allowed to germinate in the greenhouse. Four to six week old surviving plants were transferred to the field to grow to fully mature M1 plants. The mature M1 plants were allowed to self-pollinate and then seeds from the M1 plant were collected and planted to produce M2 plants.

DNA Preparation

DNA from these M2 plants was extracted and prepared in order to identify which M2 plants carried a mutation in their PG gene. The M2 plant DNA was prepared using the methods and reagents contained in the Qiagen® (Valencia, Calif.) 96 Plant Kit. Approximately 0.1 g of frozen plant sample was placed in a sample tube with a tungsten bead, frozen in liquid nitrogen and ground 2 times for 1 minute each at 20 Hz using the Qiagen® Mixer Mill MM 300. Next 400 μl solution AP1 [buffer AP1, solution DX and RNAse (100 μg/ml)] at 80° C. was added to the sample. The tube was sealed and shaken for 15 seconds. Following the addition of 130 μl buffer AP2, the tube was shaken for 15 seconds. The samples were then frozen for at least 10 minutes at minus 20° C. The samples were then centrifuged for 20 minutes at 5600×g. A 400 μl aliquot of supernatant was transferred to another sample tube. Following the addition of 600 μl of buffer AP3/E, this sample tube was capped and shaken for 15 seconds. A filter plate was placed on a square well block and 1 ml of the sample solution was applied to each well and the plate was sealed. The plate and block were centrifuged for 4 minutes at 5600×g. Next 800 μl of buffer AW was added to each well of the filter plate, sealed and spun for 15 minutes at 5600×g in the square well block. The filter plate was then placed on a new set of sample tubes and 100 μl of buffer AE was applied to the filter. It was capped and incubated at room temperature for 1 minute and then spun for 2 minutes at 5600×g. This step was repeated with an additional 100 μl buffer AE. The filter plate was removed and the filtrates were pooled and the tubes capped. Then the individual samples were normalized to a concentration of 25 ng/μl.

Tilling

The M2 DNA was pooled into groups of four or more individual plants each. For pools containing four individuals, the DNA concentration for each individual within the pool was 0.25 ng/μl with a final concentration of 1 ng/μl for the entire pool. The pooled DNA samples were arrayed on microtiter plates and subjected to gene-specific PCR.

PCR amplification was performed in 15 μl volumes containing 5 ng pooled or individual DNA, 0.75×ExTaq buffer (Panvera, Madison, Wis.), 2.6 mM MgCl2, 0.3 mM dNTPs, 0.3 μM primers, 0.05U Ex-Taq (Panvera, Madison, Wis.) DNA polymerase. PCR amplifications were performed using an MJ Research thermal cycler as follows: 95° C. for 2 minutes; 8 cycles of "touchdown PCR" (94° C. for 20 second, followed by annealing step starting at 70-68° C. for 30 seconds decreasing 1° C. per cycle, then a temperature ramp of 0.5° C. per second to 72° C. followed by 72° C. for 1 minute); 25-45 cycles of 94° C. for 20 seconds, 63-61° C. for 30 seconds, ramp 0.5° C./sec to 72° C., 72° C. for 1 minute; 72° C. for 8 minutes; 98° C. for 8 minutes; 80° C. for 20 seconds; 60 cycles of 80° C. for 7 seconds—0.3 degrees/cycle.

The PCR, primers (MWG Biotech, Inc., High Point, N.C.) were mixed as follows:

9 μl 100 μM IRD-700 labeled Left primer

1 μl 100 μM Left primer

10 μl 100 μM Right primer

The IRD-700 label can be attached to either the right or left primer. Preferably, the labeled to unlabeled primer ratio is 9:1. Alternatively, Cy5.5 modified primers or IRD-800 modified primers could be used. The label was coupled to the oligonucleotide using conventional phosphoamidite chemistry.

For digestion of 15-μL PCR products in 96-well plates, 30 μL of a solution containing 10 mM HEPES [4-(2-hydroxyethyl)-1-piperazineethanesulfonic acid] (pH 7.5), 10 mM $MgSO_4$, 0.002% (w/v) Triton X-100, 20 ng $mL^{-1}$ of bovine serum albumin, and 1/1000 dilution of CEL 1 (50 units $\mu L^{-1}$) was added with mixing on ice, and the plate was incubated at 45° C. for 15 min. CEL 1 was purified from 30 kg of celery as described by Oleykowski et al., *Nucleic Acids Res* 26: 4597-4602 (1998), except that Poros HQ rather than Mono Q was used, and the PhenylSepharose and Superdex 75 columns were omitted. The specific activity was $1\times10^6$ units $mL^{-1}$, where a unit is defined as the amount of CEL 1 required to digest 50% of 200 ng of a 500-bp DNA fragment that has a single mismatch in 50% of the duplexes. Reactions were stopped by addition of 5 μL 0.15 M EDTA (pH 8) and the mixture pipetted into wells of a spin plate (G50, Sephadex) prepared and spun according to the manufacturer's recommendations into a plate containing 1 to 1.5 μL of formamide load solution [1 mM EDTA (pH 8) and 200 μg $mL^{-1}$ bromophenol blue in deionized formamide]. The volume was reduced to a minimum by incubation at 80° C. uncovered (30-40 min) and stored on ice, then transferred to a membrane comb using a comb-loading robot (MWG Biotech). Alternatively, the DNA samples could have been concentrated using isopropanol precipitation. The comb was inserted into a slab acrylamide gel, electrophoresed for 10 min, and removed. Electrophoresis was continued for 4 h at 1,500-V, 40-W, and 40-mA limits at 50° C.

After electrophoresis, the gel was imaged using a LI-COR (Lincoln, Nebr.) scanner which was set at a channel capable of detecting the IR Dye 700 label. The gel image showed sequence-specific pattern of background bands common to all 96 lanes. Rare events, such as mutations, created a new band that stood out above the background pattern. Plants with bands indicative of mutations of interest were evaluated by sequencing individual PCR products. Plants carrying mutations confirmed by sequencing were grown up as described above (e.g., the M2 plant was backcrossed twice in order to eliminate background mutations and self-pollinated in order to create a plant that was homozygous for the mutation).

Physical and Biochemical Measurements

Tomatoes Selected for Study:

Individual tomatoes selected for study were picked from plants derived from siblings of the same cross to preserve background phenotypes as much as possible. The plants and fruit were genotyped as homozygous for the mutation, heterozygous for the mutation, or wild type. Genotyping was performed using a genetic method for determining single base pair mismatches referred to in the scientific literature as "dCAPing", see M. M Neff et al., *The Plant Journal* 14:387-392 (1998). Briefly, a degenerate PCR oligonucleotide is designed to create a restriction endonuclease recognition site when the mutant base pair is present. Plants are then simply genotyped using a PCR reaction followed by a restriction enzyme digestion and then analysis on an agarose gel.

Squeeze Test

Figure 4:
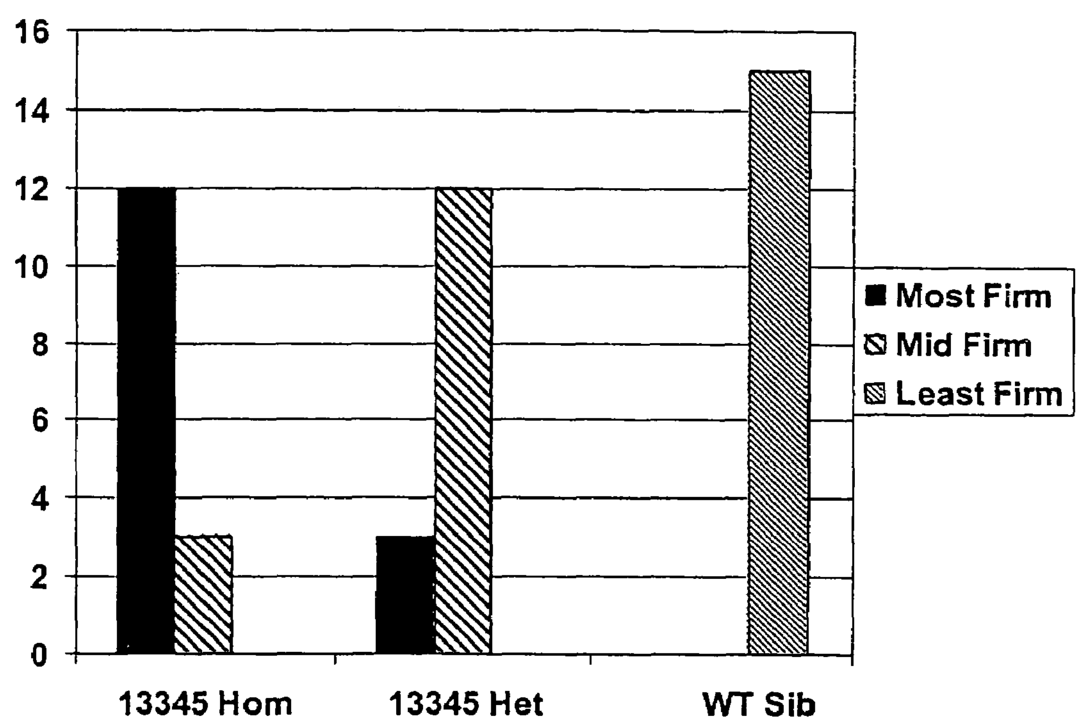
FIG. 4 is a graph of the results of a blind “squeeze” test for a tomato homozygous for PG mutation 13345 (13345 Hom), a tomato heterozygous for PG mutation 13345 (13345 Het) and a WT tomato (WT Sib).

A test was devised to simulate consumer perception of tomato fruit firmness in the three genotypes of the 13345 mutant. Fruits were evaluated at the red ripe stage. Four fruits of each genotype were blindly labeled, and 15 people were asked to rank each set as most firm, least firm, or in between (mid firm). Of the people surveyed, 80% ranked the homozygous PG mutant tomatoes as the most firm; 20% ranked the heterozygous mutant tomatoes as the most firm; and no one ranked the wild type as the most firm. Results are shown in FIG. 4.

Color Determination

Objective color values were determined for table-ripe wild type and mutant 13345 and 13342 tomatoes using a MINOLTA Color meter. Data were reported as "hue" and from 20-30 hue values were measured. Hue is the single most useful color value and the lower the hue value, the redder the tomato. In support of the idea that some characteristics associated with ripening do not differ, the results showed that PG mutants (hue values of 35.8 and 34.5) were similar in color to wild type tomatoes (hue value of 36.6).

Assays for PG Activity

Polygalacturonase enzymatic activity was measured spectrophotometrically using two different in vitro color assays that quantify the formation of reduced sugars from a polygalacturonic substrate. One assay utilized 3,5-dintrosalicylate (DNS) for color detection, and was performed as in Redenbaugh K, Hiatt W, Martineau B, Kramer M, Sheehy R, Sanders R, Houck C, and Emlay D. Safety Assessment of Genetically Engineered Fruits and Vegetables: A Case Study of the Flavr Savr Tomato. CRC Press (1992); R. Sheehy, et al., *PNAS* 85:8805-8809 (1988); Z. M. Ali and C. J. Brady, *Aust. J. Plant Physiol*. 9:155-169 (1982). The other assay utilized bicinchoninic acid (BCA) as the color substrate and was performed as in G. E. Anthon et al., *Journal of Agricultural and Food Chemistry* 50:6153-6159 (2002); and D. Fachin, et al., *Journal of Food Science* 67:1610-1615 (2002).

DNS Based Assay for PG Activity

Briefly, cell wall extracts from individual tomatoes were prepared as follows: tomatoes were sliced, locular tissue and seeds were removed, and 100 grams of the remaining tomato tissue were homogenized in 300 milliliters (ml) cold $H_2O$ and centrifuged at 4000 rpm in a tabletop centrifuge. The pellet was resuspended in 300 ml extraction buffer (1.7 M NaCl, 40 mM β-mercaptoethanol, 50 mM sodium phosphate, pH 4.6) and stirred for 4 hours at 4° C. The suspension was then centrifuged as before and the supernatant was reserved for use in the DNS color assay. Because PG enzyme is the predominant protein in the cell wall extracts, any variation in PG protein amount due to genotype would interfere with using protein concentration in the normalization process, thus in the 13345 mutant where PG protein is absent the lysates were instead normalized to wet weight of starting material.

For the color assay, 0.1 ml 2M ammonium chloride, 1 ml 1% polygalacturonic acid, and 0.1 ml cell wall extract were mixed together in tubes on ice. Samples were vortexed and a small amount was reserved as a control for the amount of reduced sugars present prior to incubation with PG enzyme. The remainder of each sample was incubated at 37° C. for 2 hours. After incubation, samples were place on ice and 0.1 ml of each was transferred to a new tube at room temperature with 0.2 ml DNS color reagent (1 g DNS/20 mls 2M NaOH, 30 g sodium potassium tartarate/50 mls warm water; the two reagents are then combined and diluted to 100 mls with warm water). Tubes were boiled in a water bath for 5 minutes and then 2 mls $H_2O$ added to each tube. Tubes were spun to clarify and then read at an absorbance of A540 on a spectrophotometer.

Figure 5:
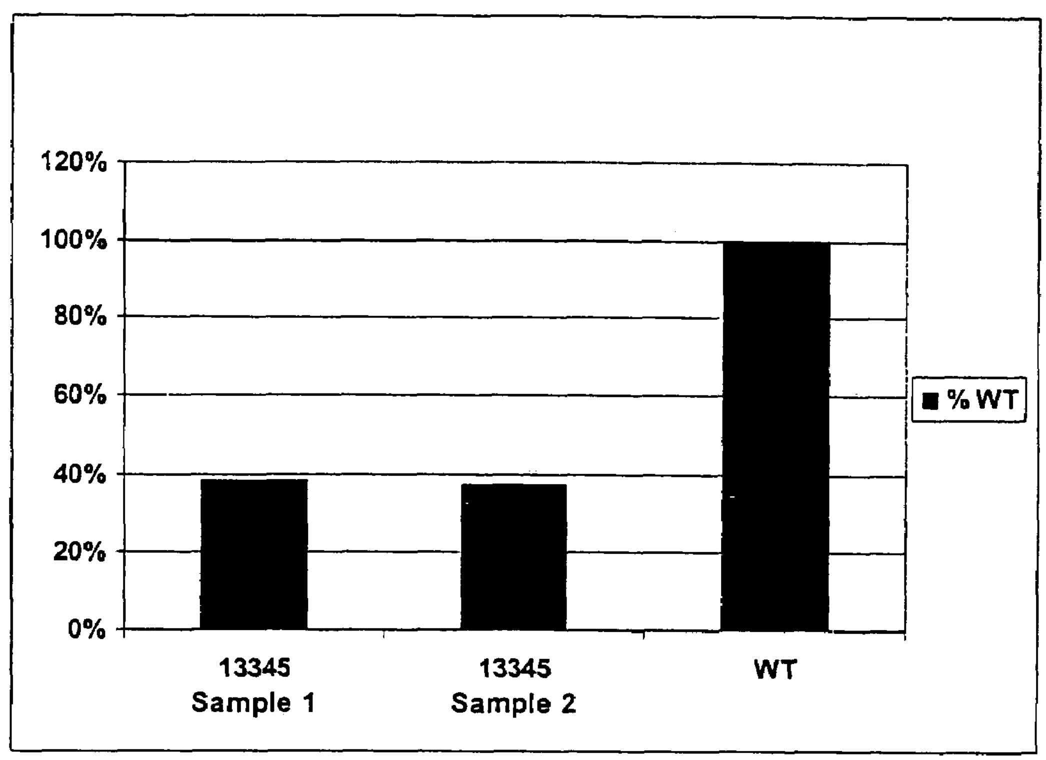
FIG. 5 is a graph of the results of the DNS based assay for PG activity.

Results of the DNS based PG activity assay, shown in FIG. 5, demonstrate that homozygous 13345 tomato fruits have less than 40% the activity of the wild type control. Tomatoes used in this assay were vine ripened and picked at equivalent stages in development.

BCA Based Assay for PG Activity

Briefly, cell wall extracts from individual tomatoes were prepared as follows: tomatoes were sliced, locular tissue and seeds were removed, and 15 g of the remaining tissue was homogenized in 30 ml cold $H_2O$. ~7.5 mls 1N HCl was added (to a final pH of 3.0), and the homogenate was spun at 4000 rpm in a tabletop centrifuge. The pellet was washed in 30 mls cold $H_2O$, and spun as before, The washed pellet was then resuspended in 7.5 mls extraction buffer (0.1M sodium phosphate pH 6.5, 1.2M NaCl) and incubated on ice for 30 minutes. The suspension was spun as before, and the supernatant was reserved for use in the BCA color assay. Again, the lysates were normalized to wet weight starting material in the 13345 mutant, and protein concentration in the 13342 mutant.

For the BCA color assay, 0.5 ml 1% polygalacturonic acid, 0.2 ml 1M NaCl, 1.3 ml $H_2O$, and 10 μL extract were mixed together and incubated at 37° C. for 30 minutes. After incubation, 1 ml carbonate buffer (54.3 g/L disodium carbonate/24.2 g/L sodium monocarbonate) was added to terminate each reaction. 0.6 mls each terminated reaction was then added to 1.9 ml $H_2O$ and 1.6 mls color reagent (equal volumes reagents A and B where reagent A is 1.96 g bicinchoninic acid/L $H_2O$ and reagent B is 1.24 g/L $CuSO_4$—$H_2O$, 1.26 g/L L-serine), and incubated at 80° C. for 30 minutes. Color development was then measured at A560 using a spectrophotometer.

Figure 6:
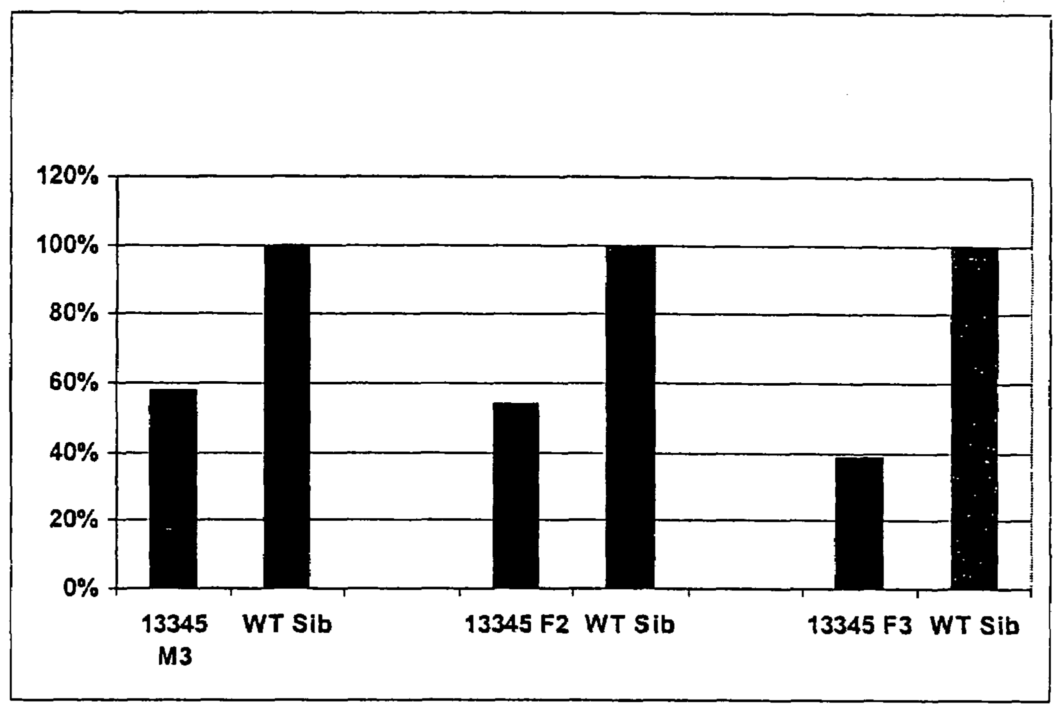
FIG. 6 is a composite graph of the results of the BCA based assay for PG activity. Panel A shows the results for different generations of tomatoes having a PG 13345 mutation. Panel B shows the results for different generations of tomatoes having a PG 13342 mutation.
Figure 6:
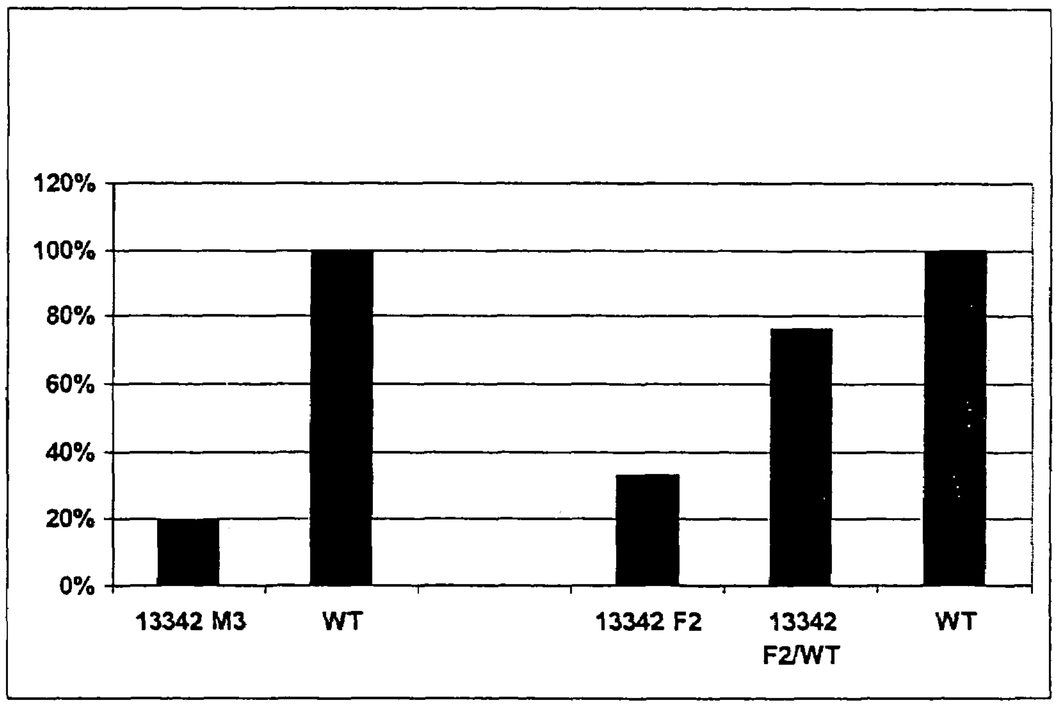

Results of the BCA based PG activity assay, shown in FIG. 6, demonstrate that both mutants exhibit decreased PG activity as compared to wild type (controls). For the 13342 mutant, tomatoes from both M3 and F2 generations of tomatoes were assayed. For the 13345 mutant, tomatoes from M3, F2 and F3 generations were assayed. These assays not only demonstrate efficacy of the mutations in decreasing PG enzymatic activity, they also demonstrate the stability of the mutations in a breeding program.

Western Blot

To ascertain the amounts of PG enzyme in the mutant tomatoes relative to wild type tomatoes, cell wall extraction lysates from the activity assays were run on SDS-PAGE gels and visualized both by Coomassie stain and by Western blot using a PG-specific polyclonal antibody as in D. DellaPenna et al., *PNAS*, 83:6420-6424 (1986). (PG antibody was a generous gift of Dr Alan Bennett, University of California, Davis).

Figure 7:
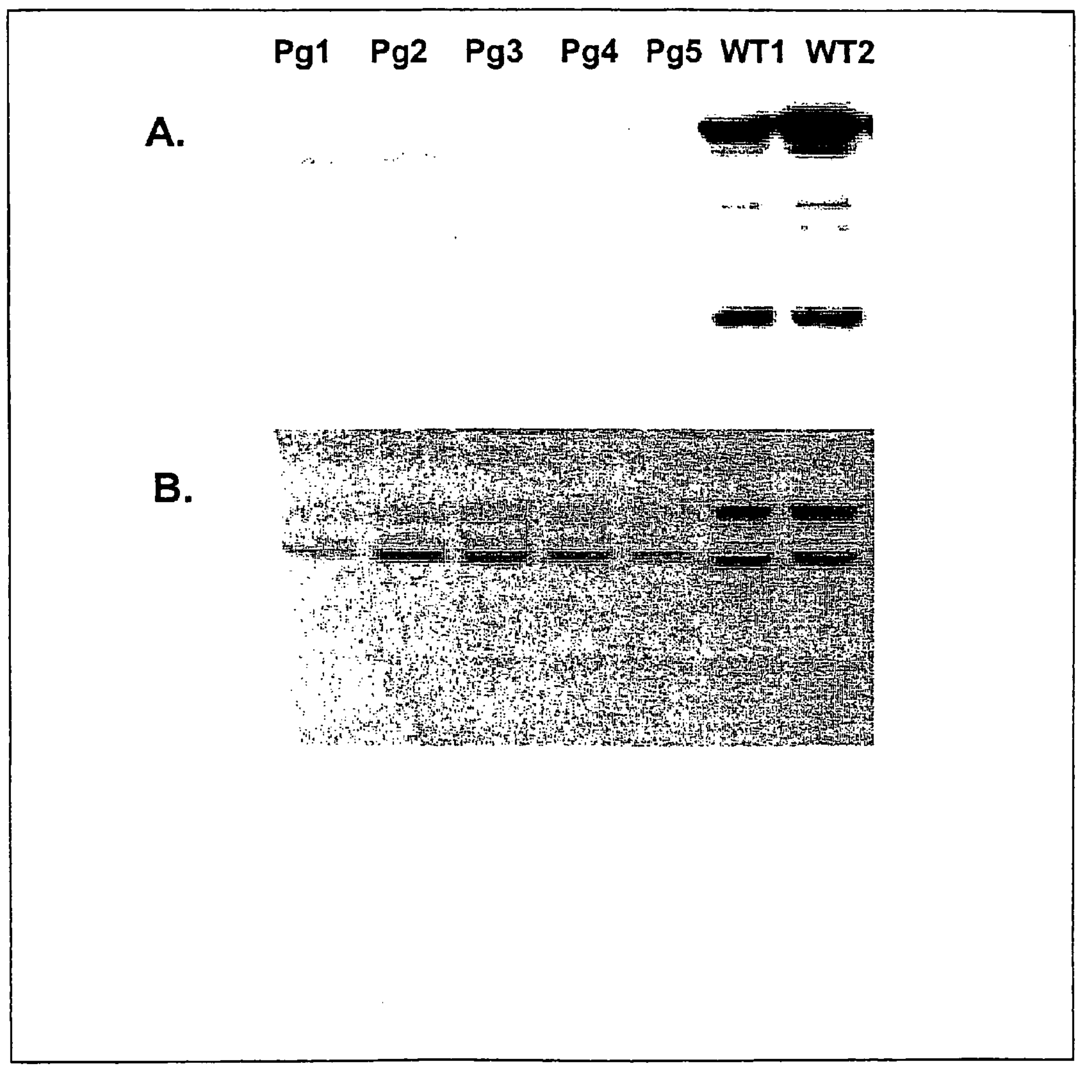
FIGS. 7A-7B show a Western blot of PG protein levels in Mutant 13345.
Figure 8:
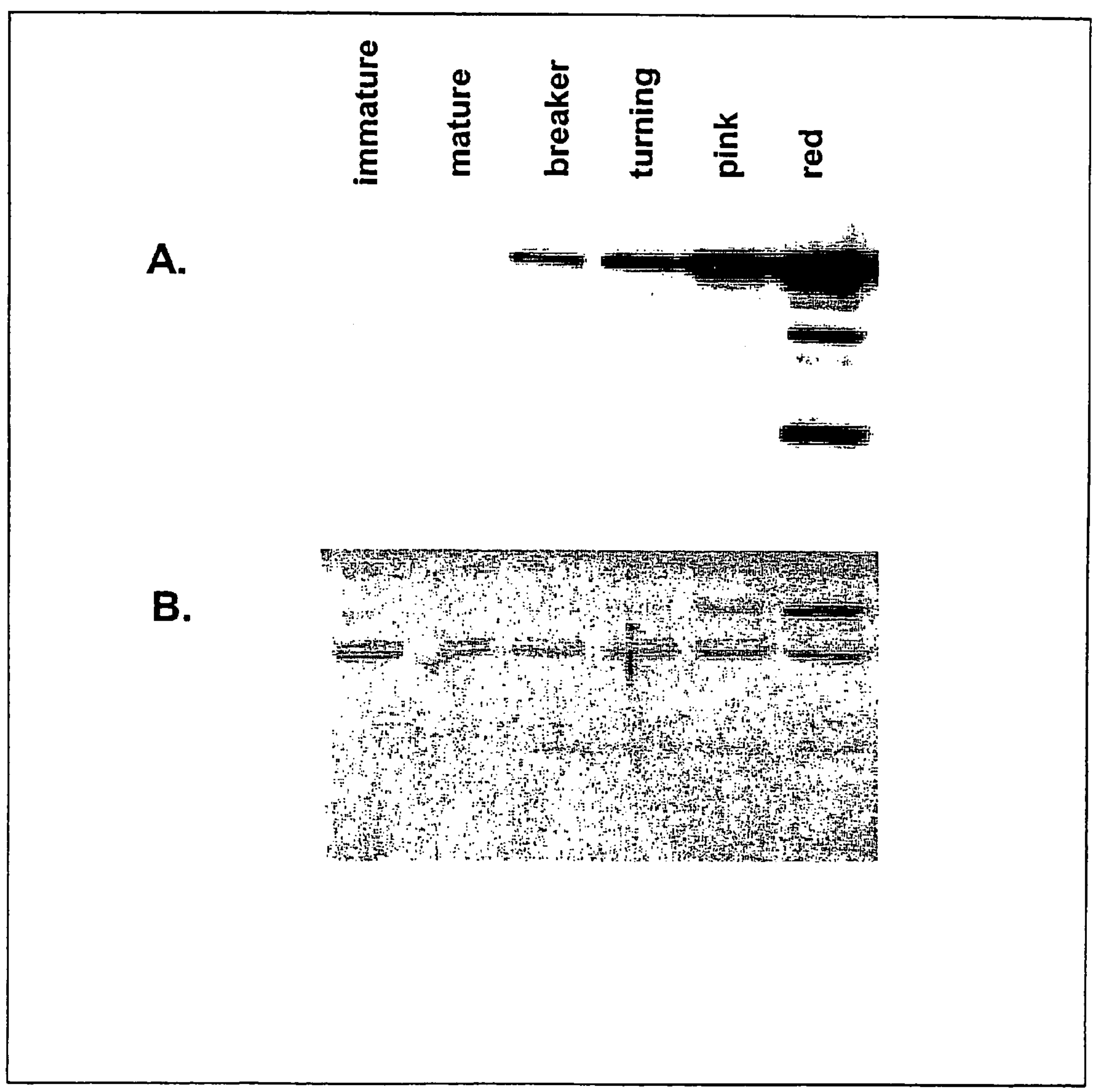
FIGS. 8A-8B show a Western blot of PG protein levels in developing Wild Type Tomatoes.
Figure 9:
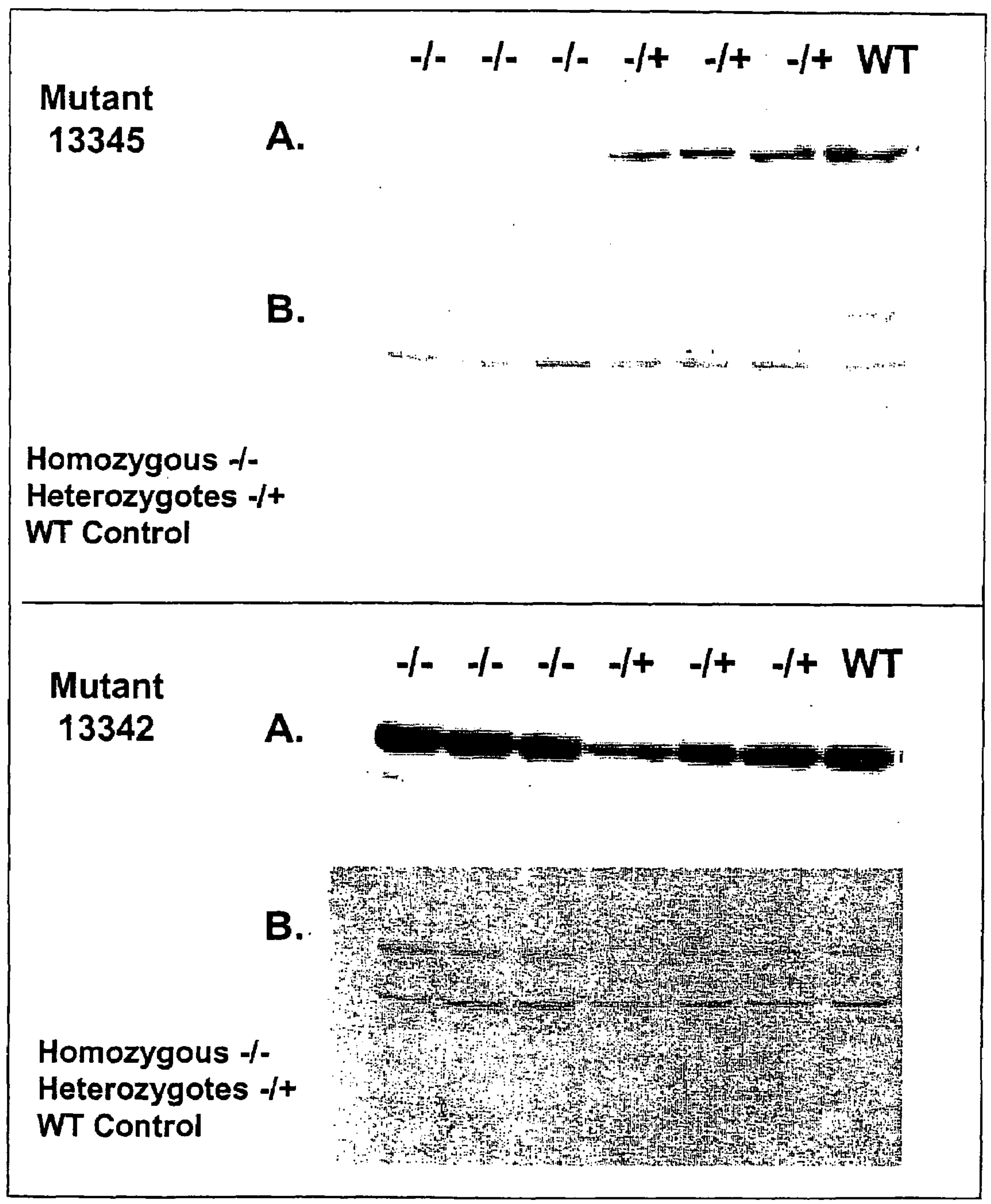
FIG. 9 shows Western blots of PG protein levels in Mutants 13345 and 13342. The upper panel shows a Western blot using PG-specific polyclonal antibody (A) and Coomassie staining (B) for cell wall extraction lysates from tomatoes with a 13345 mutation in the PG gene. The lower panel shows a Western blot using PG-specific polyclonal antibody (A) and Coomassie staining (B) for cell wall extraction lysates from tomatoes with a 13342 mutation in the PG gene.

Results of the Western blot, shown in FIG. 7, demonstrate that significantly less PG protein is detected in cell wall extraction lysates from mutant 13345 tomatoes than from wild type controls. The level of PG protein detected in red ripe mutant 13345 tomatoes is approximately that found in the early developmental stages of wild type tomatoes (FIG. 8). As shown in FIG. 9, the level of PG protein detected in red ripe mutant 13342 tomatoes is approximately the same as that found in red ripe wild type tomatoes. The Western blot results combined with the PG enzyme activity data for mutant 13342 tomatoes indicate that a non-functional form of PG protein is present in mutant 13342 tomatoes. Coomassie staining shows that PG is the predominant protein found in cell wall extraction lysates.

Identification and Evaluation of Mutation 13345

DNA from tomato plant 13345, originating from seeds of cultivar Shady Lady that were incubated in 1.2% EMS, was amplified using primer pair PGL3 (SEQ. ID. NOs. 023 and 043). The PCR amplification products were then incubated with CEL 1 and electrophoresed. The electrophoresis gel image showed a fragment at the approximate position of 204 bp, above the background pattern for the PCR amplification products. Therefore, it was likely that this fragment contained a heteroduplex created by a mutation in the PG gene. Sequence analysis of this fragment showed that the mutation was associated with a G to A change at nucleotide 1969 of SEQ. I.D. No. 1, counting A in the ATG of the START CODON as nucleotide position 1. This mutation correlates with a change from glycine to arginine at amino acid 178 of the PG polypeptide.

This mutation is within block B of the glycoside hydrolase protein family. LOGO analysis of the G178R mutation within this block revealed that the mutation lies at one of the fifteen most conserved amino acids within the family.

Tomato fruits containing Mutation 13345 exhibited lower PG enzyme activity compared to their wild type sibling, and were considered firmer than the wild type sibling.

Identification and Evaluation of Mutation 13342

Tomato plant 13342, originating from seeds of cultivar Shady Lady that were incubated in 0.6% EMS, was screened with primer pair PGL9 (SEQ. ID. NOs. 027 and 039). The PCR amplification products were then incubated with CEL 1 and electrophoresed. The electrophoresis gel image showed a fragment at the approximate position of 385 bp, above the background pattern for the PCR amplification products. Therefore, it was likely that this fragment contained a heteroduplex created by a mutation in the PG gene. Sequence analysis of this fragment showed the mutation was associated with a T to A change at nucleotide 2940 of SEQ. I.D. No. 1, counting A in the ATG of the START CODON as nucleotide position 1. This mutation correlates with a change from histidine to glutamine at amino acid 252 of the PG polypeptide.

Tomato fruits containing Mutation 13342 exhibited lower PG enzyme activity compared to their wild type sibling, and were considered firmer than their wild type sibling.

The above examples are provided to illustrate the invention but not limit its scope. Other variants of the invention will be readily apparent to one of ordinary skill in the art and are encompassed by the appended claims and all their equivalents. All publications, patents, and patent applications cited herein are hereby incorporated by reference.

We claim:

1. A method for producing a tomato plant having reduced polygalacturonase enzyme activity compared to wild type tomato plants comprising the steps of:

a) obtaining plant material from a parent tomato plant;

b) inducing at least one mutation in at least one copy of a polygalacturonase gene of the plant material by treating the plant material with a mutagen to create mutagenized plant material wherein the polygalacturonase gene is expressed in fruit;

c) culturing the mutagenized plant material to produce progeny tomato plants;

d) analyzing the progeny tomato plants to detect a mutation in at least one copy of the polygalacturonase gene of SEQ ID NO:1, wherein said mutation results in a change in amino acid 178 of SEQ ID NO: 2; and e) selecting progeny tomato plants that have a mutation in at least one copy of the polygalacturonase gene of SEQ ID NO: 1 and reduced polygalacturonase enzyme activity compared to the parent tomato plant, wherein said mutation results in a change in amino acid 178 of SEQ ID NO: 2.

2. The method of claim 1 wherein the plant material is selected from the group consisting of seeds, pollen, plant cells, and plant tissue.

3. The method of claim 1 wherein the mutagen is ethyl methanesulfonate.

4. The method of claim 3 wherein the concentration of ethyl methanesulfonate used is from about 0.4 to about 1.2%.

5. The method of claim 1 wherein step d) further includes analyzing the progeny tomato plants by i) isolating genomic DNA from the progeny tomato plants; and ii) amplifying segments of the polygalacturonase gene in the isolated genomic DNA using primers specific to the polygalacturonase gene or to the DNA sequences adjacent to the polygalacturonase gene.

6. The method of claim 1, wherein said change is having an arginine at amino acid 178.

7. The method of claim 1, wherein said mutation is a change of guanine to adenine at nucleotide 1969 of SEQ ID NO: 1.

8. A method for producing a tomato plant having reduced polygalacturonase enzyme activity compared to wild type tomato plants comprising the steps of:

a) obtaining plant material from a parent tomato plant;

b) inducing at least one mutation in at least one copy of a polygalacturonase gene of the plant material by treating the plant material with a mutagen to create mutagenized plant material wherein the polygalacturonase gene is expressed in fruit;

c) culturing the mutagenized plant material to produce progeny tomato plants;

d) analyzing the progeny tomato plants to detect a mutation in at least one copy of the polygalacturonase gene of SEQ ID NO:1, wherein said mutation results in a change in amino acid 252 of SEQ ID NO: 2; and e) selecting progeny tomato plants that have a mutation in at least one copy of the polygalacturonase gene of SEQ ID NO: 1 and reduced polygalacturonase enzyme activity compared to the parent tomato plant, wherein said mutation results in a change in amino acid 252 of SEQ ID NO: 2.

9. The method of claim 8, wherein said change is having a glutamine at amino acid 252.

10. The method of claim 8, wherein said mutation is a change of a thymine to an adenine at nucleotide 2940 of SEQ ID NO:1.

11. The method of claim 8 wherein the plant material is selected from the group consisting of seeds, pollen, plant cells, and plant tissue.

12. The method of claim 8 wherein the mutagen is ethyl methanesulfonate.

13. The method of claim 12 wherein the concentration of ethyl methanesulfonate used is from about 0.4 to about 1.2%.

14. The method of claim 8 wherein step d) further includes analyzing the progeny tomato plants by i) isolating genomic DNA from the progeny tomato plants; and ii) amplifying segments of the polygalacturonase gene in the isolated genomic DNA using primers specific to the polygalacturonase gene or to the DNA sequences adjacent to the polygalacturonase gene.

* * * * *

SEQUENCE LISTING

```
<160> NUMBER OF SEQ ID NOS: 50

<210> SEQ ID NO 1
<211> LENGTH: 7456
<212> TYPE: DNA
<213> ORGANISM: Lycopersicon esculentum
<220> FEATURE:
<221> NAME/KEY: CDS
<222> LOCATION: (1479)..(1757)
<223> OTHER INFORMATION:
<220> FEATURE:
<221> NAME/KEY: CDS
<222> LOCATION: (2416)..(2547)
<223> OTHER INFORMATION:
<220> FEATURE:
<221> NAME/KEY: CDS
<222> LOCATION: (3327)..(3491)
<223> OTHER INFORMATION:
<220> FEATURE:
<221> NAME/KEY: CDS
<222> LOCATION: (3696)..(3716)
<223> OTHER INFORMATION:
<220> FEATURE:
<221> NAME/KEY: CDS
<222> LOCATION: (4260)..(4467)
<223> OTHER INFORMATION:
<220> FEATURE:
<221> NAME/KEY: CDS
<222> LOCATION: (4567)..(4648)
<223> OTHER INFORMATION:
<220> FEATURE:
<221> NAME/KEY: CDS
<222> LOCATION: (5602)..(5710)
<223> OTHER INFORMATION:
<220> FEATURE:
<221> NAME/KEY: CDS
<222> LOCATION: (6139)..(6255)
<223> OTHER INFORMATION:
<220> FEATURE:
<221> NAME/KEY: CDS
<222> LOCATION: (6788)..(7045)
<223> OTHER INFORMATION:

<400> SEQUENCE: 1

aagcttctta aaaaggcaaa ttgattaatt tgaagtcaaa ataattaatt ataacaatgg      60

taaagcacct taagaaacca tagtttgaaa ggttaccaat gcgctatata ttaatcaact     120

tgataatata aaaaaaattt caattcgaaa agggcctaaa atattctcaa agtattcgaa     180
```

-continued

```
atggtacaaa actaccatcc gtccacctat tgactccaaa ataaaattat tatccacctt    240

tgagtttaaa attgactact tatataacaa ttctaaattt aaactatttt aatactttta    300

aaaatacatg gcgttcaaat atttaatata atttaattta tgaatatcat ttataaacca    360

accaactacc aactcattaa tcattaaatc ccacccaaat tctactatca aaattgtcct    420

aaacactact aaaacaagac gaaattgttc gagtccgaat cgaagcacca atctaattta    480

ggttgagccg catatttagg aggacacttt caatagtatt tttttcaagc atgaatttga    540

aatttaagat taatggtaaa gaagtagtac acccgaatta attcatgcct tttttaaata    600

taattatata aatatttatg atttgtttta aatattaaaa cttgaatata ttatttttaa    660

aaaaattatc tattaagtac catcacataa ttgagacgag gaataattaa gatgaacata    720

gtgtttaatt agtaatggat gggtagtaaa tttatttata aattatatca ataagttaaa    780

ttataacaaa tatttgagcg ccatgtattt taaaaaatat taaataagtt tgaatttaaa    840

accgttagat aaatggtcaa ttttgaaccc aaaagtggat gagaagggta ttttagagcc    900

aataggggga tgagaaggat attttgaagc caatatgtga tggatggagg ataattttgt    960

atcatttcta atactttaaa gatattttag gtcattttcc cttctttagt ttatagacta   1020

tagtgttagt tcatcgaata tcatctatta tttccgtctt aaattatttt ttattttata   1080

aatttttaaa aaataaatta ttttttccat ttaactttga ttgtaattaa tttttaaaaa   1140

ttaccaacat ataaataaaa ttaatattta acaaagaatt gtaacataat attttttttaa  1200

ttattcaaaa taaatatttt taaacatcat ataaaagaaa tacgacaaaa aaattgagac   1260

gggagaagac aagccagaca aaaatgtcca agaaactctt tcgtctaaat atctctcatc   1320

caaactaata taatacccat tacaattaac catattgacc aactcaaacc ccttaaaatc   1380

tataaataga caaacccttc ccatacctct tatcataaaa aaaataataa tctttttcaa   1440

tagacaagtt taaaaaccat accatataac aatatatc atg gtt atc caa agg aat  1496
                                          Met Val Ile Gln Arg Asn
                                          1               5

agt att ctc ctt ctc att att att ttt gct tca tca att tca act tgt     1544
Ser Ile Leu Leu Leu Ile Ile Ile Phe Ala Ser Ser Ile Ser Thr Cys
            10                  15                  20

aga agc aat gtt att gat gac aat tta ttc aaa caa gtt tat gat aat     1592
Arg Ser Asn Val Ile Asp Asp Asn Leu Phe Lys Gln Val Tyr Asp Asn
        25                  30                  35

att ctt gaa caa gaa ttt gct cat gat ttt caa gct tat ctt tct tat     1640
Ile Leu Glu Gln Glu Phe Ala His Asp Phe Gln Ala Tyr Leu Ser Tyr
    40                  45                  50

ttg agc aaa aat att gaa agc aac aat aat att gac aag gtt gat aaa     1688
Leu Ser Lys Asn Ile Glu Ser Asn Asn Asn Ile Asp Lys Val Asp Lys
55                  60                  65                  70

aat ggg att aaa gtg att aat gta ctt agc ttt gga gct aag ggt gat     1736
Asn Gly Ile Lys Val Ile Asn Val Leu Ser Phe Gly Ala Lys Gly Asp
                75                  80                  85

gga aaa aca tat gat aat att gtaagtattt aaatattgga atatatttgt        1787
Gly Lys Thr Tyr Asp Asn Ile
            90

ggggatgaaa atgatagaga atataagaat tatttggaag gatgaaaagt tatattttat   1847

aaagtagaaa attattttct cgtttttagt attaaggtga aaatgagttt ctcgttaagc   1907

gaggaaaagc tattttccat ggtaactgta tttttttttt acttttaata acgtcatagt   1967

atttgctata ctcaagaata agacacttat tattgatgat ttagtgctcg aaaagaaatt   2027

gatagtaatt ttgcttaata taactatcaa tttcttatat gtatattttt caaccaaaat   2087
```

-continued

```
aacaaagcgt aatccaataa gtgggcctct agaataaaga gtaagttcta ttcaattctt   2147

aaccttattt aattttagtg gaaacctcga caaaaacgaa caaacgtatt caaactttta   2207

tattcggaat tcgagaccaa ccatatgaac aacctcacac atgcatatag tcctaatata   2267

tataattttt ctaaaaaata tcttcaatct accatattga aatattgaaa aatgactttt   2327

atcctatcga acacataatc aagagtttct tttaagaatt taccactaca tttggtatgt   2387

ttcttatcgt gttaaaatta tctttcag gca ttt gag caa gca tgg aat gaa      2439
                               Ala Phe Glu Gln Ala Trp Asn Glu
                                   95                  100

gca tgt tca tct aga aca cct gtt caa ttt gtg gtt cct aaa aac aag     2487
Ala Cys Ser Ser Arg Thr Pro Val Gln Phe Val Val Pro Lys Asn Lys
            105                 110                 115

aat tat ctt ctc aag caa atc acc ttt tca ggt cca tgc aga tct tct     2535
Asn Tyr Leu Leu Lys Gln Ile Thr Phe Ser Gly Pro Cys Arg Ser Ser
        120                 125                 130

att tca gta aag gttagcatat tgattattta tatcctcttt gttagcaata         2587
Ile Ser Val Lys
    135

tattatctgg tttatgacaa aatttaagaa agtaatcaaa gatagataaa caatgaattt   2647

tcgtcactaa tttagcggat tagtgaggaa ttatcaaaat gttatgttag ctatgagcaa   2707

cttagctatg aattagctag tgaagaagtt tgatgctaat tctatttttt ttttgtagag   2767

taaagatatt tgaaacacat gtattaatta ttaattatgt cttaattaat atgtcaatgg   2827

atagttcaaa ctaaagaact gtcaaaagaa aataagaaag aaatatttat ttttaaaata   2887

aattaaaaag aaaaatatga gaaataaatt caaagcgaga aggtattaca taatctatgg   2947

ggataaaagg atattatata tgtaagaaaa cagcactaca catatctaat aaagtctcat   3007

aaatggatat aaaaaatagt gtgtaagcaa cagttatccc tacaaaaact tttgtggggt   3067

agatcgatcc agaggttgtt tccagactct tgcttaaaaa aaatgttttt tctaaataag   3127

tttgaaagaa atgttatatg atgaaaatat gaagaaaaac atatcaatat taaaaataat   3187

aaagtaatca aagtaaacga aataacaata ggaataatac tcataaatga aaatttagtg   3247

gcttttcgtt aacataatct tagtttattc attgtttctt taatttccct tcttattttt   3307

tttgaaatta ctaatgcag att ttt gga tcc tta gaa gca tct agt aaa att    3359
                     Ile Phe Gly Ser Leu Glu Ala Ser Ser Lys Ile
                             140                 145

tca gac tac aaa gat aga agg ctt tgg att gct ttt gat agt gtt caa     3407
Ser Asp Tyr Lys Asp Arg Arg Leu Trp Ile Ala Phe Asp Ser Val Gln
    150                 155                 160

aat tta gtt gtt gga gga gga gga act atc aat ggc aat gga caa gta     3455
Asn Leu Val Val Gly Gly Gly Gly Thr Ile Asn Gly Asn Gly Gln Val
165                 170                 175                 180

tgg tgg cca agt tct tgc aaa ata aat aaa tca ctg gtaattttat          3501
Trp Trp Pro Ser Ser Cys Lys Ile Asn Lys Ser Leu
                185                 190

aaccttgctt ataagtttta cgctatgttg ctcgaattct ttaaacttgt tctaaagata   3561

ttatatattt gaaggaggtg tcacaaatgc atcacatttt tagagattcc gaccaatatt   3621

agttttatgt aatctaattt tcagagcatc tttgccttgt actgatcatt gttacccttt   3681

ttttcttcat gcag cca tgc agg gat gca cca acg gtacgttaat tgcatttgat   3736
                Pro Cys Arg Asp Ala Pro Thr
                            195

ttgataaaaa aaaaaagcct aaaatatatt tgaattttaa ttgaaaggtt ataataattc   3796

ttaactttgg gcaggaccta ttaccccttg cactatttaa tagtgtattt taaagatata   3856
```

-continued

```
aaagtgttta gttgaaacaa aaatttagat attcaaaaac tatttgaaaa ttactataaa   3916

ttgcaatttt tttgcatatc aatatgatta aaaaatatta gttaaagttc ttatgatttg   3976

attctaaaaa taaaaatcat gacaaacaat agtagacgga gaaagtatat aacaatacct   4036

cttcaagtag aatcgatttg tacacacacc tcaaaaccta cgttttcttc gatttatatt   4096

tcctatttct tttaatagta atcaaaggct attagttctg tcaaaatcta tacattggaa   4156

actctatctt tgacgcctcg tacattcgag atcgttgaac aatggatgaa tgattattta   4216

actttgtatt taaatattaa aactaatatt gtttaatttt cag gcc tta acc ttc     4271
                                                Ala Leu Thr Phe
                                                200

tgg aat tgc aaa aat ttg aaa gtg aat aat cta aag agt aaa aat gca     4319
Trp Asn Cys Lys Asn Leu Lys Val Asn Asn Leu Lys Ser Lys Asn Ala
    205                 210                 215

caa caa att cat atc aaa ttt gag tca tgc act aat gtt gta gct tca     4367
Gln Gln Ile His Ile Lys Phe Glu Ser Cys Thr Asn Val Val Ala Ser
220                 225                 230                 235

aat ttg atg atc aat gct tca gca aag agc cca aat act gat gga gtc     4415
Asn Leu Met Ile Asn Ala Ser Ala Lys Ser Pro Asn Thr Asp Gly Val
                240                 245                 250

cat gta tca aat act caa tat att caa ata tct gat act att att gga     4463
His Val Ser Asn Thr Gln Tyr Ile Gln Ile Ser Asp Thr Ile Ile Gly
            255                 260                 265

aca g gtttatttat ttaattttta tttatccaat ttaattagaa aaaaaaagga       4517
Thr

gtatttttat ttgataacta aattattaat ttttaatttt tttttatag gt  gat gat   4574
                                                      Gly Asp Asp
                                                          270

tgt att tca att gtt tct gga tct caa aat gtg cag gcc aca aat att     4622
Cys Ile Ser Ile Val Ser Gly Ser Gln Asn Val Gln Ala Thr Asn Ile
            275                 280                 285

act tgt ggt cca ggt cat ggt ata ag  gtactctatt ttacaaatat           4668
Thr Cys Gly Pro Gly His Gly Ile Ser
        290                 295

acttgtttcc attttctcta tttcataaaa ggtagtatga tataataatt actttaaatc   4728

ctttaattaa tttattggca aattttttct cttgtcttta tggttaatga cttagcacaa   4788

taattagggc cgtttggatg ggcgaataaa agcagcttta aaaaagtact tttaaaagtg   4848

ttgaaactta tttttaaaat aagcagttat cggtttggat aaaagtgctg aagttgttat   4908

gtcaaacgtg aaaagggaaa aatggaagaa agaaatgtta gggttatatg ggttatttgt   4968

ataaaaatat taagcacaaa aagataaaaa tgtggtcaac ttaaaacaac ttataagcta   5028

ccctacccta ccccagcttt taacttttgg cttaaaataa gttttttttt ttaaaactta   5088

aaataagttg ttttgagtat tgccaaagag ctaaataatg caaaaaccag cttttaagtc   5148

agtttgacca gcttttaagc tgagccaaac aggctcttaa aatgtctgct tagatgtgct   5208

atatatattt gagctttttt tgaagtagta tattatcctt aagttcaaca taaaatacat   5268

gctttaacat agcacatata gttaatcaaa agacgaaatg atgaataatt ttgcgaattt   5328

gattattcac aagaaaaggg atagttcaaa gtgtacattt caatgaattg aagatatcat   5388

aaagactaaa attagaagaa tcaataattg agggatcaaa aatgttatta ccttattaaa   5448

atactattcc attttcatat taaattaact aattaagagt gttttataat ctaataaaac   5508

atgcaataat tattgacgaa atgtggtttt ggtacctata atctttctga atatttgctc   5568
```

-continued

```
tatttttct ctttttattt ttccatggat tac t att gga agc tta gga tct      5620
                                      Ile Gly Ser Leu Gly Ser
                                                  300

gga aat tca gaa gct tat gtg tct aat gtt act gta aat gaa gcc aaa    5668
Gly Asn Ser Glu Ala Tyr Val Ser Asn Val Thr Val Asn Glu Ala Lys
        305                 310                 315

att atc ggt gcc gaa aat gga gtt agg atc aag act tgg cag            5710
Ile Ile Gly Ala Glu Asn Gly Val Arg Ile Lys Thr Trp Gln
    320                 325                 330

gtaccctccc cccccccccc ccccccacag gcccattttt ttaatttttt ttaaattttt  5770

attcgaatat caatattaaa gattaatttg atttcatgtt tgaaatttat atttggataa  5830

agtatgtatt ttactagctt tctatgttat atagaaaaaa aaatgttcag aacttcagat  5890

tattgtactc gtactaagtg taaatgtgtt gctttgttta gaagtttggt ttatccagtt  5950

ttgggtcatg attaaaccaa acttataatg aaaaggggct gcaacggccg gcccactagt  6010

gctagtatca ataggaagat ctcacgtctg tttattcaga tggacgttct tggttgaatg  6070

ttaataatta taaatttaat taacatgtaa ttaagcatta tataaattaa tgtggtttaa  6130

taatgtag gga gga tct gga caa gct agc aac atc aaa ttt ctg aat gtg   6180
         Gly Gly Ser Gly Gln Ala Ser Asn Ile Lys Phe Leu Asn Val
                 335                 340                 345

gaa atg caa gac gtt aag tat ccc ata att ata gac caa aac tat tgt    6228
Glu Met Gln Asp Val Lys Tyr Pro Ile Ile Ile Asp Gln Asn Tyr Cys
            350                 355                 360

gat cga gtt gaa cca tgt ata caa cag gtaatttttt attaacgaac          6275
Asp Arg Val Glu Pro Cys Ile Gln Gln
        365                 370

aatttattat attttattac ttcttaaatc accttacatc attaaaactt tgagattctt  6335

ttcactagtt agtaactttt tgaatagatt tttagtaaat gatattcatt attcctttta  6395

tttttcttct aatttatgga tcttttggac tatggtctaa aaatcttgtt aaagtaaact  6455

gaatatcata agaaaaaatg ttagattata atctaaattt tttataaatt attagacgtt  6515

atctaatatt ttgtatgtaa gattgagaaa catatacata aaacattaga ttcaaattta  6575

ataaatatcta aaatattgat tcaaatcaat catgactaca caaacgaata catgcagatt  6635

ctcaaacata tagatgaagt catttcaaaa cgaatcaaat atagtagagt atatccttaa  6695

aagagagcat ttgggtaaat aagtaaaaat cattaagtta taaaaaaaat tctaactcga  6755

tctctcacga ttatttaatc actttgttcc ag ttt tca gca gtt caa gtg aaa    6808
                                    Phe Ser Ala Val Gln Val Lys
                                                375

aat gtg gtg tat gag aat atc aag ggc aca agt gca aca aag gtg gcc    6856
Asn Val Val Tyr Glu Asn Ile Lys Gly Thr Ser Ala Thr Lys Val Ala
    380                 385                 390

ata aaa ttt gat tgc agc aca aac ttt cca tgt gaa gga att ata atg    6904
Ile Lys Phe Asp Cys Ser Thr Asn Phe Pro Cys Glu Gly Ile Ile Met
395                 400                 405                 410

gag aat ata aat tta gta ggg gaa agt gga aaa cca tca gag gct acg    6952
Glu Asn Ile Asn Leu Val Gly Glu Ser Gly Lys Pro Ser Glu Ala Thr
                415                 420                 425

tgc aaa aat gtc cat ttt aac aat gct gaa cat gtt aca cca cac tgc    7000
Cys Lys Asn Val His Phe Asn Asn Ala Glu His Val Thr Pro His Cys
            430                 435                 440

act tca cta gaa att tca gag gat gaa gct ctt ttg tat aat tat        7045
Thr Ser Leu Glu Ile Ser Glu Asp Glu Ala Leu Leu Tyr Asn Tyr
        445                 450                 455

taatttatac tatagatctt caatatatag cagatatgat atatcacaat aaacaaatct  7105
```

atatctatgt attgaataat tattattaat atgtacggat tgaagtttta ataagactac 7165 tatgtatttc tattttctag tcaaaagttt gacgattgta ctttttaatg tacaaaaata 7225 ataaaatggt tatttatatg atgtatatat ccctttggta tttcttgttg aactataatg 7285 tcattattta ataactatta tctgtgcaat gattgtattt gttaatgata cataatatat 7345 ctttcatcat tgataataag aataaaatat tttacgtcta ttactttgtg aattatatgt 7405 agattttagt ttttgtttta tttttaatta aaccgagtga aatataaaga g 7456

<210> SEQ ID NO 2
<211> LENGTH: 457
<212> TYPE: PRT
<213> ORGANISM: Lycopersicon esculentum

<400> SEQUENCE: 2

```
Met Val Ile Gln Arg Asn Ser Ile Leu Leu Leu Ile Ile Ile Phe Ala
1               5                   10                  15

Ser Ser Ile Ser Thr Cys Arg Ser Asn Val Ile Asp Asp Asn Leu Phe
            20                  25                  30

Lys Gln Val Tyr Asp Asn Ile Leu Glu Gln Glu Phe Ala His Asp Phe
        35                  40                  45

Gln Ala Tyr Leu Ser Tyr Leu Ser Lys Asn Ile Glu Ser Asn Asn Asn
    50                  55                  60

Ile Asp Lys Val Asp Lys Asn Gly Ile Lys Val Ile Asn Val Leu Ser
65                  70                  75                  80

Phe Gly Ala Lys Gly Asp Gly Lys Thr Tyr Asp Asn Ile Ala Phe Glu
                85                  90                  95

Gln Ala Trp Asn Glu Ala Cys Ser Ser Arg Thr Pro Val Gln Phe Val
            100                 105                 110

Val Pro Lys Asn Lys Asn Tyr Leu Leu Lys Gln Ile Thr Phe Ser Gly
        115                 120                 125

Pro Cys Arg Ser Ser Ile Ser Val Lys Ile Phe Gly Ser Leu Glu Ala
    130                 135                 140

Ser Ser Lys Ile Ser Asp Tyr Lys Asp Arg Arg Leu Trp Ile Ala Phe
145                 150                 155                 160

Asp Ser Val Gln Asn Leu Val Val Gly Gly Gly Gly Thr Ile Asn Gly
                165                 170                 175

Asn Gly Gln Val Trp Trp Pro Ser Ser Cys Lys Ile Asn Lys Ser Leu
            180                 185                 190

Pro Cys Arg Asp Ala Pro Thr Ala Leu Thr Phe Trp Asn Cys Lys Asn
        195                 200                 205

Leu Lys Val Asn Asn Leu Lys Ser Lys Asn Ala Gln Gln Ile His Ile
    210                 215                 220

Lys Phe Glu Ser Cys Thr Asn Val Val Ala Ser Asn Leu Met Ile Asn
225                 230                 235                 240

Ala Ser Ala Lys Ser Pro Asn Thr Asp Gly Val His Val Ser Asn Thr
                245                 250                 255

Gln Tyr Ile Gln Ile Ser Asp Thr Ile Ile Gly Thr Gly Asp Asp Cys
            260                 265                 270

Ile Ser Ile Val Ser Gly Ser Gln Asn Val Gln Ala Thr Asn Ile Thr
        275                 280                 285

Cys Gly Pro Gly His Gly Ile Ser Ile Gly Ser Leu Gly Ser Gly Asn
    290                 295                 300

Ser Glu Ala Tyr Val Ser Asn Val Thr Val Asn Glu Ala Lys Ile Ile
```

-continued

```
305                 310                 315                 320

Gly Ala Glu Asn Gly Val Arg Ile Lys Thr Trp Gln Gly Gly Ser Gly
                325                 330                 335

Gln Ala Ser Asn Ile Lys Phe Leu Asn Val Glu Met Gln Asp Val Lys
            340                 345                 350

Tyr Pro Ile Ile Ile Asp Gln Asn Tyr Cys Asp Arg Val Glu Pro Cys
        355                 360                 365

Ile Gln Gln Phe Ser Ala Val Gln Val Lys Asn Val Val Tyr Glu Asn
    370                 375                 380

Ile Lys Gly Thr Ser Ala Thr Lys Val Ala Ile Lys Phe Asp Cys Ser
385                 390                 395                 400

Thr Asn Phe Pro Cys Glu Gly Ile Ile Met Glu Asn Ile Asn Leu Val
                405                 410                 415

Gly Glu Ser Gly Lys Pro Ser Glu Ala Thr Cys Lys Asn Val His Phe
            420                 425                 430

Asn Asn Ala Glu His Val Thr Pro His Cys Thr Ser Leu Glu Ile Ser
        435                 440                 445

Glu Asp Glu Ala Leu Leu Tyr Asn Tyr
    450                 455


<210> SEQ ID NO 3
<211> LENGTH: 25
<212> TYPE: DNA
<213> ORGANISM: Lycopersicon esculentum

<400> SEQUENCE: 3

ttgagacggg agaagacaag ccaga                                        25


<210> SEQ ID NO 4
<211> LENGTH: 28
<212> TYPE: DNA
<213> ORGANISM: Lycopersicon esculentum

<400> SEQUENCE: 4

ccaaccatat gaacaacctc acacatgc                                     28


<210> SEQ ID NO 5
<211> LENGTH: 26
<212> TYPE: DNA
<213> ORGANISM: Lycopersicon esculentum

<400> SEQUENCE: 5

tgtggggtag atcgatccag aggttg                                       26


<210> SEQ ID NO 6
<211> LENGTH: 25
<212> TYPE: DNA
<213> ORGANISM: Lycopersicon esculentum

<400> SEQUENCE: 6

acgcctcgta cattcgagat cgttg                                        25


<210> SEQ ID NO 7
<211> LENGTH: 27
<212> TYPE: DNA
<213> ORGANISM: Lycopersicon esculentum

<400> SEQUENCE: 7

tcacaagaaa agggatagtt caaagtg                                      27
```

-continued

<210> SEQ ID NO 8
<211> LENGTH: 26
<212> TYPE: DNA
<213> ORGANISM: Lycopersicon esculentum

<400> SEQUENCE: 8
tgaagtcatt tcaaaacgaa tcaaat 26

<210> SEQ ID NO 9
<211> LENGTH: 32
<212> TYPE: DNA
<213> ORGANISM: Lycopersicon esculentum

<400> SEQUENCE: 9
ttctccttct cattattatt tttgcttcat ca 32

<210> SEQ ID NO 10
<211> LENGTH: 30
<212> TYPE: DNA
<213> ORGANISM: Lycopersicon esculentum

<400> SEQUENCE: 10
ctggaattgc aaaaatttga aagtgaataa 30

<210> SEQ ID NO 11
<211> LENGTH: 26
<212> TYPE: DNA
<213> ORGANISM: Lycopersicon esculentum

<400> SEQUENCE: 11
ttgagacggg agaagacaag ccagac 26

<210> SEQ ID NO 12
<211> LENGTH: 27
<212> TYPE: DNA
<213> ORGANISM: Lycopersicon esculentum

<400> SEQUENCE: 12
agtggctttc gtactacata atcttag 27

<210> SEQ ID NO 13
<211> LENGTH: 28
<212> TYPE: DNA
<213> ORGANISM: Lycopersicon esculentum

<400> SEQUENCE: 13
catgcaataa ttattgacga aatgtggt 28

<210> SEQ ID NO 14
<211> LENGTH: 25
<212> TYPE: DNA
<213> ORGANISM: Lycopersicon esculentum

<400> SEQUENCE: 14
ttgagacggg agaagacaag ccaga 25

<210> SEQ ID NO 15
<211> LENGTH: 25
<212> TYPE: DNA
<213> ORGANISM: Lycopersicon esculentum

<400> SEQUENCE: 15
tgagacggga gaagacaagc cagac 25

-continued

<210> SEQ ID NO 16
<211> LENGTH: 32
<212> TYPE: DNA
<213> ORGANISM: Lycopersicon esculentum

<400> SEQUENCE: 16
ttctccttct cattattatt tttgcttcat ca 32

<210> SEQ ID NO 17
<211> LENGTH: 30
<212> TYPE: DNA
<213> ORGANISM: Lycopersicon esculentum

<400> SEQUENCE: 17
ctggaattgc aaaaatttga aagtgaataa 30

<210> SEQ ID NO 18
<211> LENGTH: 33
<212> TYPE: DNA
<213> ORGANISM: Lycopersicon esculentum

<400> SEQUENCE: 18
ttgacgaaat gtggttttgg tacctataat ctt 33

<210> SEQ ID NO 19
<211> LENGTH: 30
<212> TYPE: DNA
<213> ORGANISM: Lycopersicon esculentum

<400> SEQUENCE: 19
cacaaacgaa tacatgcaga ttctcaaaca 30

<210> SEQ ID NO 20
<211> LENGTH: 28
<212> TYPE: DNA
<213> ORGANISM: Lycopersicon esculentum

<400> SEQUENCE: 20
ccaaccatat gaacaacctc acacatgc 28

<210> SEQ ID NO 21
<211> LENGTH: 28
<212> TYPE: DNA
<213> ORGANISM: Lycopersicon esculentum

<400> SEQUENCE: 21
atcttcaatc taccatattg aaatattg 28

<210> SEQ ID NO 22
<211> LENGTH: 26
<212> TYPE: DNA
<213> ORGANISM: Lycopersicon esculentum

<400> SEQUENCE: 22
tacatttggt agtgtttctt atcgtg 26

<210> SEQ ID NO 23
<211> LENGTH: 27
<212> TYPE: DNA
<213> ORGANISM: Lycopersicon esculentum

<400> SEQUENCE: 23

-continued agtggctttc gtactacata atcttag 27

<210> SEQ ID NO 24
<211> LENGTH: 32
<212> TYPE: DNA
<213> ORGANISM: Lycopersicon esculentum

<400> SEQUENCE: 24
caaaagacga aatgatgaat aattttgcga at 32

<210> SEQ ID NO 25
<211> LENGTH: 30
<212> TYPE: DNA
<213> ORGANISM: Lycopersicon esculentum

<400> SEQUENCE: 25
cacaaacgaa tacatgcaga ttctcaaaca 30

<210> SEQ ID NO 26
<211> LENGTH: 26
<212> TYPE: DNA
<213> ORGANISM: Lycopersicon esculentum

<400> SEQUENCE: 26
agtagagtat atccttaaaa gagagc 26

<210> SEQ ID NO 27
<211> LENGTH: 25
<212> TYPE: DNA
<213> ORGANISM: Lycopersicon esculentum

<400> SEQUENCE: 27
acgcctctga cattcgagat cgttg 25

<210> SEQ ID NO 28
<211> LENGTH: 27
<212> TYPE: DNA
<213> ORGANISM: Lycopersicon esculentum

<400> SEQUENCE: 28
ccatggaaaa tagcttttcc tcgctta 27

<210> SEQ ID NO 29
<211> LENGTH: 30
<212> TYPE: DNA
<213> ORGANISM: Lycopersicon esculentum

<400> SEQUENCE: 29
cattttgata attcctcact aatccgctaa 30

<210> SEQ ID NO 30
<211> LENGTH: 25
<212> TYPE: DNA
<213> ORGANISM: Lycopersicon esculentum

<400> SEQUENCE: 30
caaggggtaa taggtcctgc ccaaa 25

<210> SEQ ID NO 31
<211> LENGTH: 25
<212> TYPE: DNA
<213> ORGANISM: Lycopersicon esculentum

<400> SEQUENCE: 31
ctgcttttat tcgcccatcc aaacg 25

<210> SEQ ID NO 32
<211> LENGTH: 30
<212> TYPE: DNA
<213> ORGANISM: Lycopersicon esculentum

<400> SEQUENCE: 32
gaatctcaaa gttttaatga tgtaaggtga 30

<210> SEQ ID NO 33
<211> LENGTH: 29
<212> TYPE: DNA
<213> ORGANISM: Lycopersicon esculentum

<400> SEQUENCE: 33
ttatacaaaa gagcttcatc ctctgaaat 29

<210> SEQ ID NO 34
<211> LENGTH: 31
<212> TYPE: DNA
<213> ORGANISM: Lycopersicon esculentum

<400> SEQUENCE: 34
cctgttgtat acatggttca actcgatcac a 31

<210> SEQ ID NO 35
<211> LENGTH: 31
<212> TYPE: DNA
<213> ORGANISM: Lycopersicon esculentum

<400> SEQUENCE: 35
cctctgaaat ttctagtgaa gtgcagtgtg g 31

<210> SEQ ID NO 36
<211> LENGTH: 28
<212> TYPE: DNA
<213> ORGANISM: Lycopersicon esculentum

<400> SEQUENCE: 36
tccatggaaa atgactttcc tcgcttac 28

<210> SEQ ID NO 37
<211> LENGTH: 31
<212> TYPE: DNA
<213> ORGANISM: Lycopersicon esculentum

<400> SEQUENCE: 37
atagaagatc tgcatggacc tgaaaaggtg a 31

<210> SEQ ID NO 38
<211> LENGTH: 29
<212> TYPE: DNA
<213> ORGANISM: Lycopersicon esculentum

<400> SEQUENCE: 38
aagtaatatt tgtggcctgc acatttgag 29

<210> SEQ ID NO 39
<211> LENGTH: 35
<212> TYPE: DNA
<213> ORGANISM: Lycopersicon esculentum

<400> SEQUENCE: 39
cctaattatt gtgctaagtc attaaccata aagac 35

<210> SEQ ID NO 40
<211> LENGTH: 36
<212> TYPE: DNA
<213> ORGANISM: Lycopersicon esculentum

<400> SEQUENCE: 40
gaccatagtc caaaagatcc ataaattaga agaaaa 36

<210> SEQ ID NO 41
<211> LENGTH: 36
<212> TYPE: DNA
<213> ORGANISM: Lycopersicon esculentum

<400> SEQUENCE: 41
tgacattata gttcaacaag aaataccaaa gggata 36

<210> SEQ ID NO 42
<211> LENGTH: 28
<212> TYPE: DNA
<213> ORGANISM: Lycopersicon esculentum

<400> SEQUENCE: 42
accatggaaa atagctttcc tcgcttaa 28

<210> SEQ ID NO 43
<211> LENGTH: 25
<212> TYPE: DNA
<213> ORGANISM: Lycopersicon esculentum

<400> SEQUENCE: 43
caaaggggta atagtcctgc ccaaa 25

<210> SEQ ID NO 44
<211> LENGTH: 26
<212> TYPE: DNA
<213> ORGANISM: Lycopersicon esculentum

<400> SEQUENCE: 44
ctacttttat tacgcccatc caaacg 26

<210> SEQ ID NO 45
<211> LENGTH: 34
<212> TYPE: DNA
<213> ORGANISM: Lycopersicon esculentum

<400> SEQUENCE: 45
aagtgtaaat gtgttgcttt gtttagaagt ttgg 34

<210> SEQ ID NO 46
<211> LENGTH: 36
<212> TYPE: DNA
<213> ORGANISM: Lycopersicon esculentum

<400> SEQUENCE: 46
tgaaaagaat ctcaaagttt taatgatgta aggtga 36

<210> SEQ ID NO 47
<211> LENGTH: 7456
<212> TYPE: DNA
<213> ORGANISM: Lycopersicon esculentum
<220> FEATURE:
<221> NAME/KEY: CDS
<222> LOCATION: (1479)..(1757)
<223> OTHER INFORMATION:
<220> FEATURE:
<221> NAME/KEY: CDS
<222> LOCATION: (2416)..(2547)
<223> OTHER INFORMATION:
<220> FEATURE:
<221> NAME/KEY: CDS
<222> LOCATION: (3327)..(3491)
<223> OTHER INFORMATION:
<220> FEATURE:
<221> NAME/KEY: CDS
<222> LOCATION: (3696)..(3716)
<223> OTHER INFORMATION:
<220> FEATURE:
<221> NAME/KEY: CDS
<222> LOCATION: (4260)..(4467)
<223> OTHER INFORMATION:
<220> FEATURE:
<221> NAME/KEY: CDS
<222> LOCATION: (4567)..(4648)
<223> OTHER INFORMATION:
<220> FEATURE:
<221> NAME/KEY: CDS
<222> LOCATION: (5602)..(5710)
<223> OTHER INFORMATION:
<220> FEATURE:
<221> NAME/KEY: CDS
<222> LOCATION: (6139)..(6255)
<223> OTHER INFORMATION:
<220> FEATURE:
<221> NAME/KEY: CDS
<222> LOCATION: (6788)..(7045)
<223> OTHER INFORMATION:

<400> SEQUENCE: 47

```
aagcttctta aaaaggcaaa ttgattaatt tgaagtcaaa ataattaatt ataacaatgg     60

taaagcacct taagaaacca tagtttgaaa ggttaccaat gcgctatata ttaatcaact    120

tgataatata aaaaaaattt caattcgaaa agggcctaaa atattctcaa agtattcgaa    180

atggtacaaa actaccatcc gtccacctat tgactccaaa ataaaattat tatccacctt    240

tgagtttaaa attgactact tatataacaa ttctaaattt aaactatttt aatactttta    300

aaaatacatg gcgttcaaat atttaatata atttaattta tgaatatcat ttataaacca    360

accaactacc aactcattaa tcattaaatc ccacccaaat tctactatca aaattgtcct    420

aaacactact aaaacaagac gaaattgttc gagtccgaat cgaagcacca atctaattta    480

ggttgagccg catatttagg aggacacttt caatagtatt tttttcaagc atgaatttga    540

aatttaagat taatggtaaa gaagtagtac acccgaatta attcatgcct tttttaaata    600

taattatata aatatttatg atttgtttta aatattaaaa cttgaatata ttatttttaa    660

aaaaattatc tattaagtac catcacataa ttgagacgag gaataattaa gatgaacata    720

gtgtttaatt agtaatggat gggtagtaaa tttatttata aattatatca ataagttaaa    780

ttataacaaa tatttgagcg ccatgtattt taaaaaatat taaataagtt tgaatttaaa    840

accgttagat aaatggtcaa ttttgaaccc aaaagtggat gagaagggta ttttagagcc    900

aataggggga tgagaaggat attttgaagc caatatgtga tggatggagg ataattttgt    960

atcatttcta atactttaaa gatattttag gtcattttcc cttctttagt ttatagacta   1020

tagtgttagt tcatcgaata tcatctatta tttccgtctt aaattatttt ttattttata   1080

aatttttaaa aaataaatta ttttttccat ttaactttga ttgtaattaa tttttaaaaa   1140

ttaccaacat ataaataaaa ttaatattta acaaagaatt gtaacataat atttttttaa   1200
```

-continued

```
ttattcaaaa taaatatttt taaacatcat ataaaagaaa tacgacaaaa aaattgagac   1260

gggagaagac aagccagaca aaaatgtcca agaaactctt tcgtctaaat atctctcatc   1320

caaactaata taatacccat tacaattaac catattgacc aactcaaacc ccttaaaatc   1380

tataaataga caaacccttc ccatacctct tatcataaaa aaaataataa tctttttcaa   1440

tagacaagtt taaaaaccat accatataac aatatatc atg gtt atc caa agg aat   1496
                                          Met Val Ile Gln Arg Asn
                                          1               5

agt att ctc ctt ctc att att att ttt gct tca tca att tca act tgt     1544
Ser Ile Leu Leu Leu Ile Ile Ile Phe Ala Ser Ser Ile Ser Thr Cys
            10                  15                  20

aga agc aat gtt att gat gac aat tta ttc aaa caa gtt tat gat aat     1592
Arg Ser Asn Val Ile Asp Asp Asn Leu Phe Lys Gln Val Tyr Asp Asn
        25                  30                  35

att ctt gaa caa gaa ttt gct cat gat ttt caa gct tat ctt tct tat     1640
Ile Leu Glu Gln Glu Phe Ala His Asp Phe Gln Ala Tyr Leu Ser Tyr
    40                  45                  50

ttg agc aaa aat att gaa agc aac aat aat att gac aag gtt gat aaa     1688
Leu Ser Lys Asn Ile Glu Ser Asn Asn Asn Ile Asp Lys Val Asp Lys
55                  60                  65                  70

aat ggg att aaa gtg att aat gta ctt agc ttt gga gct aag ggt gat     1736
Asn Gly Ile Lys Val Ile Asn Val Leu Ser Phe Gly Ala Lys Gly Asp
                75                  80                  85

gga aaa aca tat gat aat att gtaagtattt aaatattgga atatatttgt       1787
Gly Lys Thr Tyr Asp Asn Ile
            90

ggggatgaaa atgatagaga atataagaat tatttggaag gatgaaaagt tatattttat   1847

aaagtagaaa attattttct cgtttttagt attaaggtga aaatgagttt ctcgttaagc   1907

gaggaaaagc tattttccat ggtaactgta tttttttttt acttttaata acgtcatagt   1967

atttgctata ctcaagaata agacacttat tattgatgat ttagtgctcg aaaagaaatt   2027

gatagtaatt ttgcttaata taactatcaa tttcttatat gtatattttt caaccaaaat   2087

aacaaagcgt aatccaataa gtgggcctct agaataaaga gtaagttcta ttcaattctt   2147

aaccttattt aattttagtg gaaacctcga caaaaacgaa caaacgtatt caaactttta   2207

tattcggaat tcgagaccaa ccatatgaac aacctcacac atgcatatag tcctaatata   2267

tataattttt ctaaaaaata tcttcaatct accatattga aatattgaaa aatgactttt   2327

atcctatcga acacataatc aagagtttct tttaagaatt taccactaca tttggtatgt   2387

ttcttatcgt gttaaaatta tctttcag gca ttt gag caa gca tgg aat gaa     2439
                              Ala Phe Glu Gln Ala Trp Asn Glu
                                  95                  100

gca tgt tca tct aga aca cct gtt caa ttt gtg gtt cct aaa aac aag     2487
Ala Cys Ser Ser Arg Thr Pro Val Gln Phe Val Val Pro Lys Asn Lys
            105                 110                 115

aat tat ctt ctc aag caa atc acc ttt tca ggt cca tgc aga tct tct     2535
Asn Tyr Leu Leu Lys Gln Ile Thr Phe Ser Gly Pro Cys Arg Ser Ser
        120                 125                 130

att tca gta aag gttagcatat tgattattta tatcctcttt gttagcaata        2587
Ile Ser Val Lys
    135

tattatctgg tttatgacaa aatttaagaa agtaatcaaa gatagataaa caatgaattt   2647

tcgtcactaa tttagcggat tagtgaggaa ttatcaaaat gttatgttag ctatgagcaa   2707

cttagctatg aattagctag tgaagaagtt tgatgctaat tctatttttt ttttgtagag   2767

taaagatatt tgaaacacat gtattaatta ttaattatgt cttaattaat atgtcaatgg   2827
```

-continued

```
atagttcaaa ctaaagaact gtcaaaagaa aataagaaag aaatatttat ttttaaaata   2887

aattaaaaag aaaaatatga gaaataaatt caaagcgaga aggtattaca taatctatgg   2947

ggataaaagg atattatata tgtaagaaaa cagcactaca catatctaat aaagtctcat   3007

aaatggatat aaaaaatagt gtgtaagcaa cagttatccc tacaaaaact tttgtggggt   3067

agatcgatcc agaggttgtt tccagactct tgcttaaaaa aaatgttttt tctaaataag   3127

tttgaaagaa atgttatatg atgaaaatat gaagaaaaac atatcaatat taaaaataat   3187

aaagtaatca aagtaaacga aataacaata ggaataatac tcataaatga aaatttagtg   3247

gcttttcgtt aacataatct tagtttattc attgtttctt taatttccct tcttattttt   3307

tttgaaatta ctaatgcag att ttt gga tcc tta gaa gca tct agt aaa att   3359
                    Ile Phe Gly Ser Leu Glu Ala Ser Ser Lys Ile
                            140                 145

tca gac tac aaa gat aga agg ctt tgg att gct ttt gat agt gtt caa   3407
Ser Asp Tyr Lys Asp Arg Arg Leu Trp Ile Ala Phe Asp Ser Val Gln
    150                 155                 160

aat tta gtt gtt gga gga gga gga act atc aat ggc aat aga caa gta   3455
Asn Leu Val Val Gly Gly Gly Gly Thr Ile Asn Gly Asn Arg Gln Val
165                 170                 175                 180

tgg tgg cca agt tct tgc aaa ata aat aaa tca ctg gtaattttat        3501
Trp Trp Pro Ser Ser Cys Lys Ile Asn Lys Ser Leu
                185                 190

aaccttgctt ataagtttta cgctatgttg ctcgaattct ttaaacttgt tctaaagata   3561

ttatatattt gaaggaggtg tcacaaatgc atcacatttt tagagattcc gaccaatatt   3621

agttttatgt aatctaattt tcagagcatc tttgccttgt actgatcatt gttacccttt   3681

ttttcttcat gcag cca tgc agg gat gca cca acg gtacgttaat tgcatttgat   3736
                Pro Cys Arg Asp Ala Pro Thr
                        195

ttgataaaaa aaaaaagcct aaaatatatt tgaattttaa ttgaaaggtt ataataattc   3796

ttaactttgg gcaggaccta ttaccccttg cactatttaa tagtgtattt taaagatata   3856

aaagtgttta gttgaaacaa aaatttagat attcaaaaac tatttgaaaa ttactataaa   3916

ttgcaatttt tttgcatatc aatatgatta aaaaatatta gttaaagttc ttatgatttg   3976

attctaaaaa taaaaatcat gacaaacaat agtagacgga gaaagtatat aacaatacct   4036

cttcaagtag aatcgatttg tacacacacc tcaaaaccta cgttttcttc gatttatatt   4096

tcctatttct tttaatagta atcaaaggct attagttctg tcaaaatcta tacattggaa   4156

actctatctt tgacgcctcg tacattcgag atcgttgaac aatggatgaa tgattattta   4216

actttgtatt taaatattaa aactaatatt gtttaatttt cag gcc tta acc ttc     4271
                                               Ala Leu Thr Phe
                                               200

tgg aat tgc aaa aat ttg aaa gtg aat aat cta aag agt aaa aat gca   4319
Trp Asn Cys Lys Asn Leu Lys Val Asn Asn Leu Lys Ser Lys Asn Ala
    205                 210                 215

caa caa att cat atc aaa ttt gag tca tgc act aat gtt gta gct tca   4367
Gln Gln Ile His Ile Lys Phe Glu Ser Cys Thr Asn Val Val Ala Ser
220                 225                 230                 235

aat ttg atg atc aat gct tca gca aag agc cca aat act gat gga gtc   4415
Asn Leu Met Ile Asn Ala Ser Ala Lys Ser Pro Asn Thr Asp Gly Val
                240                 245                 250

cat gta tca aat act caa tat att caa ata tct gat act att att gga   4463
His Val Ser Asn Thr Gln Tyr Ile Gln Ile Ser Asp Thr Ile Ile Gly
            255                 260                 265
```

-continued

```
aca g gtttatttat ttaattttta tttatccaat ttaattagaa aaaaaaagga        4517
Thr

gtatttttat ttgataacta aattattaat ttttaatttt tttttatag gt  gat gat   4574
                                                          Gly Asp Asp
                                                              270

tgt att tca att gtt tct gga tct caa aat gtg cag gcc aca aat att     4622
Cys Ile Ser Ile Val Ser Gly Ser Gln Asn Val Gln Ala Thr Asn Ile
            275                 280                 285

act tgt ggt cca ggt cat ggt ata ag  gtactctatt ttacaaatat           4668
Thr Cys Gly Pro Gly His Gly Ile Ser
        290                 295

acttgtttcc attttctcta tttcataaaa ggtagtatga tataataatt actttaaatc   4728

ctttaattaa tttattggca aattttttct cttgtcttta tggttaatga cttagcacaa   4788

taattagggc cgtttggatg ggcgaataaa agcagcttta aaaaagtact tttaaaagtg   4848

ttgaaactta tttttaaaat aagcagttat cggtttggat aaaagtgctg aagttgttat   4908

gtcaaacgtg aaaagggaaa aatggaagaa agaaatgtta gggttatatg ggttatttgt   4968

ataaaaatat taagcacaaa aagataaaaa tgtggtcaac ttaaaacaac ttataagcta   5028

ccctacccta ccccagcttt taacttttgg cttaaaataa gttttttttt ttaaaactta   5088

aaataagttg ttttgagtat tgccaaagag ctaaataatg caaaaaccag cttttaagtc   5148

agtttgacca gcttttaagc tgagccaaac aggctcttaa aatgtctgct tagatgtgct   5208

atatatattt gagctttttt tgaagtagta tattatcctt aagttcaaca taaaatacat   5268

gctttaacat agcacatata gttaatcaaa agacgaaatg atgaataatt ttgcgaattt   5328

gattattcac aagaaaaggg atagttcaaa gtgtacattt caatgaattg aagatatcat   5388

aaagactaaa attagaagaa tcaataattg agggatcaaa aatgttatta ccttattaaa   5448

atactattcc attttcatat taaattaact aattaagagt gttttataat ctaataaaac   5508

atgcaataat tattgacgaa atgtggtttt ggtacctata atctttctga atatttgctc   5568

tatttttttct cttttttattt ttccatggat tac t att gga agc tta gga tct    5620
                                         Ile Gly Ser Leu Gly Ser
                                                     300

gga aat tca gaa gct tat gtg tct aat gtt act gta aat gaa gcc aaa     5668
Gly Asn Ser Glu Ala Tyr Val Ser Asn Val Thr Val Asn Glu Ala Lys
        305                 310                 315

att atc ggt gcc gaa aat gga gtt agg atc aag act tgg cag             5710
Ile Ile Gly Ala Glu Asn Gly Val Arg Ile Lys Thr Trp Gln
    320                 325                 330

gtaccctccc cccccccccc ccccccacag gcccattttt ttaatttttt ttaaattttt   5770

attcgaatat caatattaaa gattaatttg atttcatgtt tgaaatttat atttggataa   5830

agtatgtatt ttactagctt tctatgttat atagaaaaaa aaatgttcag aacttcagat   5890

tattgtactc gtactaagtg taaatgtgtt gctttgttta gaagtttggt ttatccagtt   5950

ttgggtcatg attaaaccaa acttataatg aaaaggggct gcaacggccg gcccactagt   6010

gctagtatca ataggaagat ctcacgtctg tttattcaga tggacgttct tggttgaatg   6070

ttaataatta taaatttaat taacatgtaa ttaagcatta tataaattaa tgtggtttaa   6130

taatgtag gga gga tct gga caa gct agc aac atc aaa ttt ctg aat gtg    6180
         Gly Gly Ser Gly Gln Ala Ser Asn Ile Lys Phe Leu Asn Val
                 335                 340                 345

gaa atg caa gac gtt aag tat ccc ata att ata gac caa aac tat tgt     6228
Glu Met Gln Asp Val Lys Tyr Pro Ile Ile Ile Asp Gln Asn Tyr Cys
            350                 355                 360
```

-continued

```
gat cga gtt gaa cca tgt ata caa cag gtaatttttt attaacgaac          6275
Asp Arg Val Glu Pro Cys Ile Gln Gln
        365                 370

aatttattat attttattac ttcttaaatc accttacatc attaaaactt tgagattctt   6335

ttcactagtt agtaactttt tgaatagatt tttagtaaat gatattcatt attcctttta   6395

tttttcttct aatttatgga tcttttggac tatggtctaa aaatcttgtt aaagtaaact   6455

gaatatcata agaaaaaatg ttagattata atctaaattt tttataaatt attagacgtt   6515

atctaatatt ttgtatgtaa gattgagaaa catatacata aaacattaga ttcaaattta   6575

ataaatatcta aaatattgat tcaaatcaat catgactaca caaacgaata catgcagatt  6635

ctcaaacata tagatgaagt catttcaaaa cgaatcaaat atagtagagt atatccttaa   6695

aagagagcat ttgggtaaat aagtaaaaat cattaagtta taaaaaaaat tctaactcga   6755

tctctcacga ttatttaatc actttgttcc ag ttt tca gca gtt caa gtg aaa     6808
                                    Phe Ser Ala Val Gln Val Lys
                                                375

aat gtg gtg tat gag aat atc aag ggc aca agt gca aca aag gtg gcc     6856
Asn Val Val Tyr Glu Asn Ile Lys Gly Thr Ser Ala Thr Lys Val Ala
    380                 385                 390

ata aaa ttt gat tgc agc aca aac ttt cca tgt gaa gga att ata atg     6904
Ile Lys Phe Asp Cys Ser Thr Asn Phe Pro Cys Glu Gly Ile Ile Met
395                 400                 405                 410

gag aat ata aat tta gta ggg gaa agt gga aaa cca tca gag gct acg     6952
Glu Asn Ile Asn Leu Val Gly Glu Ser Gly Lys Pro Ser Glu Ala Thr
                415                 420                 425

tgc aaa aat gtc cat ttt aac aat gct gaa cat gtt aca cca cac tgc     7000
Cys Lys Asn Val His Phe Asn Asn Ala Glu His Val Thr Pro His Cys
            430                 435                 440

act tca cta gaa att tca gag gat gaa gct ctt ttg tat aat tat         7045
Thr Ser Leu Glu Ile Ser Glu Asp Glu Ala Leu Leu Tyr Asn Tyr
        445                 450                 455

taatttatac tatagatctt caatatatag cagatatgat atatcacaat aaacaaatct   7105

atatctatgt attgaataat tattattaat atgtacggat tgaagtttta ataagactac   7165

tatgtatttc tattttctag tcaaaagttt gacgattgta ctttttaatg tacaaaaata   7225

ataaaatggt tatttatatg atgtatatat ccctttggta tttcttgttg aactataatg   7285

tcattattta ataactatta tctgtgcaat gattgtattt gttaatgata cataatatat   7345

ctttcatcat tgataataag aataaaatat tttacgtcta ttactttgtg aattatatgt   7405

agattttagt ttttgtttta tttttaatta aaccgagtga aatataaaga g            7456


<210> SEQ ID NO 48
<211> LENGTH: 457
<212> TYPE: PRT
<213> ORGANISM: Lycopersicon esculentum

<400> SEQUENCE: 48

Met Val Ile Gln Arg Asn Ser Ile Leu Leu Leu Ile Ile Ile Phe Ala
1               5                   10                  15

Ser Ser Ile Ser Thr Cys Arg Ser Asn Val Ile Asp Asp Asn Leu Phe
            20                  25                  30

Lys Gln Val Tyr Asp Asn Ile Leu Glu Gln Glu Phe Ala His Asp Phe
        35                  40                  45

Gln Ala Tyr Leu Ser Tyr Leu Ser Lys Asn Ile Glu Ser Asn Asn Asn
    50                  55                  60

Ile Asp Lys Val Asp Lys Asn Gly Ile Lys Val Ile Asn Val Leu Ser
```

-continued

```
65                  70                  75                  80

Phe Gly Ala Lys Gly Asp Gly Lys Thr Tyr Asp Asn Ile Ala Phe Glu
                85                  90                  95

Gln Ala Trp Asn Glu Ala Cys Ser Ser Arg Thr Pro Val Gln Phe Val
            100                 105                 110

Val Pro Lys Asn Lys Asn Tyr Leu Leu Lys Gln Ile Thr Phe Ser Gly
        115                 120                 125

Pro Cys Arg Ser Ser Ile Ser Val Lys Ile Phe Gly Ser Leu Glu Ala
    130                 135                 140

Ser Ser Lys Ile Ser Asp Tyr Lys Asp Arg Arg Leu Trp Ile Ala Phe
145                 150                 155                 160

Asp Ser Val Gln Asn Leu Val Val Gly Gly Gly Gly Thr Ile Asn Gly
                165                 170                 175

Asn Arg Gln Val Trp Trp Pro Ser Ser Cys Lys Ile Asn Lys Ser Leu
            180                 185                 190

Pro Cys Arg Asp Ala Pro Thr Ala Leu Thr Phe Trp Asn Cys Lys Asn
        195                 200                 205

Leu Lys Val Asn Asn Leu Lys Ser Lys Asn Ala Gln Gln Ile His Ile
    210                 215                 220

Lys Phe Glu Ser Cys Thr Asn Val Val Ala Ser Asn Leu Met Ile Asn
225                 230                 235                 240

Ala Ser Ala Lys Ser Pro Asn Thr Asp Gly Val His Val Ser Asn Thr
                245                 250                 255

Gln Tyr Ile Gln Ile Ser Asp Thr Ile Ile Gly Thr Gly Asp Asp Cys
            260                 265                 270

Ile Ser Ile Val Ser Gly Ser Gln Asn Val Gln Ala Thr Asn Ile Thr
        275                 280                 285

Cys Gly Pro Gly His Gly Ile Ser Ile Gly Ser Leu Gly Ser Gly Asn
    290                 295                 300

Ser Glu Ala Tyr Val Ser Asn Val Thr Val Asn Glu Ala Lys Ile Ile
305                 310                 315                 320

Gly Ala Glu Asn Gly Val Arg Ile Lys Thr Trp Gln Gly Gly Ser Gly
                325                 330                 335

Gln Ala Ser Asn Ile Lys Phe Leu Asn Val Glu Met Gln Asp Val Lys
            340                 345                 350

Tyr Pro Ile Ile Ile Asp Gln Asn Tyr Cys Asp Arg Val Glu Pro Cys
        355                 360                 365

Ile Gln Gln Phe Ser Ala Val Gln Val Lys Asn Val Val Tyr Glu Asn
    370                 375                 380

Ile Lys Gly Thr Ser Ala Thr Lys Val Ala Ile Lys Phe Asp Cys Ser
385                 390                 395                 400

Thr Asn Phe Pro Cys Glu Gly Ile Ile Met Glu Asn Ile Asn Leu Val
                405                 410                 415

Gly Glu Ser Gly Lys Pro Ser Glu Ala Thr Cys Lys Asn Val His Phe
            420                 425                 430

Asn Asn Ala Glu His Val Thr Pro His Cys Thr Ser Leu Glu Ile Ser
        435                 440                 445

Glu Asp Glu Ala Leu Leu Tyr Asn Tyr
    450                 455

<210> SEQ ID NO 49
<211> LENGTH: 7456
<212> TYPE: DNA
<213> ORGANISM: Lycopersicon esculentum
```

<220> FEATURE:
<221> NAME/KEY: CDS
<222> LOCATION: (1479)..(1757)
<223> OTHER INFORMATION:
<220> FEATURE:
<221> NAME/KEY: CDS
<222> LOCATION: (2416)..(2547)
<223> OTHER INFORMATION:
<220> FEATURE:
<221> NAME/KEY: CDS
<222> LOCATION: (3327)..(3491)
<223> OTHER INFORMATION:
<220> FEATURE:
<221> NAME/KEY: CDS
<222> LOCATION: (3696)..(3716)
<223> OTHER INFORMATION:
<220> FEATURE:
<221> NAME/KEY: CDS
<222> LOCATION: (4260)..(4467)
<223> OTHER INFORMATION:
<220> FEATURE:
<221> NAME/KEY: CDS
<222> LOCATION: (4567)..(4648)
<223> OTHER INFORMATION:
<220> FEATURE:
<221> NAME/KEY: CDS
<222> LOCATION: (5602)..(5710)
<223> OTHER INFORMATION:
<220> FEATURE:
<221> NAME/KEY: CDS
<222> LOCATION: (6139)..(6255)
<223> OTHER INFORMATION:
<220> FEATURE:
<221> NAME/KEY: CDS
<222> LOCATION: (6788)..(7045)
<223> OTHER INFORMATION:

<400> SEQUENCE: 49

```
aagcttctta aaaaggcaaa ttgattaatt tgaagtcaaa ataattaatt ataacaatgg     60

taaagcacct taagaaacca tagtttgaaa ggttaccaat gcgctatata ttaatcaact    120

tgataatata aaaaaaattt caattcgaaa agggcctaaa atattctcaa agtattcgaa    180

atggtacaaa actaccatcc gtccacctat tgactccaaa ataaaattat tatccacctt    240

tgagtttaaa attgactact tatataacaa ttctaaattt aaactatttt aatactttta    300

aaaatacatg gcgttcaaat atttaatata atttaattta tgaatatcat ttataaacca    360

accaactacc aactcattaa tcattaaatc ccacccaaat tctactatca aaattgtcct    420

aaacactact aaaacaagac gaaattgttc gagtccgaat cgaagcacca atctaattta    480

ggttgagccg catatttagg aggacacttt caatagtatt tttttcaagc atgaatttga    540

aatttaagat taatggtaaa gaagtagtac acccgaatta attcatgcct tttttaaata    600

taattatata aatatttatg atttgtttta aatattaaaa cttgaatata ttatttttaa    660

aaaaattatc tattaagtac catcacataa ttgagacgag gaataattaa gatgaacata    720

gtgtttaatt agtaatggat gggtagtaaa tttatttata aattatatca ataagttaaa    780

ttataacaaa tatttgagcg ccatgtattt taaaaaatat taaataagtt tgaatttaaa    840

accgttagat aaatggtcaa ttttgaaccc aaaagtggat gagaagggta ttttagagcc    900

aataggggga tgagaaggat attttgaagc caatatgtga tggatggagg ataattttgt    960

atcatttcta atactttaaa gatattttag gtcattttcc cttctttagt ttatagacta   1020

tagtgttagt tcatcgaata tcatctatta tttccgtctt aaattatttt ttattttata   1080

aatttttaaa aaataaatta ttttttccat ttaactttga ttgtaattaa tttttaaaaa   1140

ttaccaacat ataaataaaa ttaatattta acaaagaatt gtaacataat attttttaa   1200
```

-continued

```
ttattcaaaa taaatatttt taaacatcat ataaaagaaa tacgacaaaa aaattgagac   1260

gggagaagac aagccagaca aaaatgtcca agaaactctt tcgtctaaat atctctcatc   1320

caaactaata taatacccat tacaattaac catattgacc aactcaaacc ccttaaaatc   1380

tataaataga caaacccttc ccatacctct tatcataaaa aaaataataa tctttttcaa   1440

tagacaagtt taaaaaccat accatataac aatatatc atg gtt atc caa agg aat   1496
                                          Met Val Ile Gln Arg Asn
                                          1               5

agt att ctc ctt ctc att att att ttt gct tca tca att tca act tgt     1544
Ser Ile Leu Leu Leu Ile Ile Ile Phe Ala Ser Ser Ile Ser Thr Cys
            10                  15                  20

aga agc aat gtt att gat gac aat tta ttc aaa caa gtt tat gat aat     1592
Arg Ser Asn Val Ile Asp Asp Asn Leu Phe Lys Gln Val Tyr Asp Asn
        25                  30                  35

att ctt gaa caa gaa ttt gct cat gat ttt caa gct tat ctt tct tat     1640
Ile Leu Glu Gln Glu Phe Ala His Asp Phe Gln Ala Tyr Leu Ser Tyr
    40                  45                  50

ttg agc aaa aat att gaa agc aac aat aat att gac aag gtt gat aaa     1688
Leu Ser Lys Asn Ile Glu Ser Asn Asn Asn Ile Asp Lys Val Asp Lys
55                  60                  65                  70

aat ggg att aaa gtg att aat gta ctt agc ttt gga gct aag ggt gat     1736
Asn Gly Ile Lys Val Ile Asn Val Leu Ser Phe Gly Ala Lys Gly Asp
                75                  80                  85

gga aaa aca tat gat aat att gtaagtattt aaatattgga atatatttgt        1787
Gly Lys Thr Tyr Asp Asn Ile
            90

ggggatgaaa atgatagaga atataagaat tatttggaag gatgaaaagt tatattttat   1847

aaagtagaaa attattttct cgtttttagt attaaggtga aaatgagttt ctcgttaagc   1907

gaggaaaagc tattttccat ggtaactgta tttttttttt acttttaata acgtcatagt   1967

atttgctata ctcaagaata agacacttat tattgatgat ttagtgctcg aaaagaaatt   2027

gatagtaatt ttgcttaata taactatcaa tttcttatat gtatattttt caaccaaaat   2087

aacaaagcgt aatccaataa gtgggcctct agaataaaga gtaagttcta ttcaattctt   2147

aaccttattt aattttagtg gaaacctcga caaaaacgaa caaacgtatt caaactttta   2207

tattcggaat tcgagaccaa ccatatgaac aacctcacac atgcatatag tcctaatata   2267

tataattttt ctaaaaaata tcttcaatct accatattga aatattgaaa aatgactttt   2327

atcctatcga acacataatc aagagtttct tttaagaatt taccactaca tttggtatgt   2387

ttcttatcgt gttaaaatta tctttcag gca ttt gag caa gca tgg aat gaa      2439
                               Ala Phe Glu Gln Ala Trp Asn Glu
                                   95                  100

gca tgt tca tct aga aca cct gtt caa ttt gtg gtt cct aaa aac aag     2487
Ala Cys Ser Ser Arg Thr Pro Val Gln Phe Val Val Pro Lys Asn Lys
            105                 110                 115

aat tat ctt ctc aag caa atc acc ttt tca ggt cca tgc aga tct tct     2535
Asn Tyr Leu Leu Lys Gln Ile Thr Phe Ser Gly Pro Cys Arg Ser Ser
        120                 125                 130

att tca gta aag gttagcatat tgattattta tatcctcttt gttagcaata         2587
Ile Ser Val Lys
    135

tattatctgg tttatgacaa aatttaagaa agtaatcaaa gatagataaa caatgaattt   2647

tcgtcactaa tttagcggat tagtgaggaa ttatcaaaat gttatgttag ctatgagcaa   2707

cttagctatg aattagctag tgaagaagtt tgatgctaat tctatttttt ttttgtagag   2767

taaagatatt tgaaacacat gtattaatta ttaattatgt cttaattaat atgtcaatgg   2827
```

-continued

```
atagttcaaa ctaaagaact gtcaaaagaa aataagaaag aaatatttat ttttaaaata   2887

aattaaaaag aaaaatatga gaaataaatt caaagcgaga aggtattaca taatctatgg   2947

ggataaaagg atattatata tgtaagaaaa cagcactaca catatctaat aaagtctcat   3007

aaatggatat aaaaaatagt gtgtaagcaa cagttatccc tacaaaaact tttgtggggt   3067

agatcgatcc agaggttgtt tccagactct tgcttaaaaa aaatgttttt tctaaataag   3127

tttgaaagaa atgttatatg atgaaaatat gaagaaaaac atatcaatat taaaaataat   3187

aaagtaatca aagtaaacga aataacaata ggaataatac tcataaatga aaatttagtg   3247

gcttttcgtt aacataatct tagtttattc attgtttctt taatttccct tcttattttt   3307

tttgaaatta ctaatgcag att ttt gga tcc tta gaa gca tct agt aaa att    3359
                     Ile Phe Gly Ser Leu Glu Ala Ser Ser Lys Ile
                             140                 145

tca gac tac aaa gat aga agg ctt tgg att gct ttt gat agt gtt caa     3407
Ser Asp Tyr Lys Asp Arg Arg Leu Trp Ile Ala Phe Asp Ser Val Gln
    150                 155                 160

aat tta gtt gtt gga gga gga gga act atc aat ggc aat gga caa gta     3455
Asn Leu Val Val Gly Gly Gly Gly Thr Ile Asn Gly Asn Gly Gln Val
165                 170                 175                 180

tgg tgg cca agt tct tgc aaa ata aat aaa tca ctg gtaattttat          3501
Trp Trp Pro Ser Ser Cys Lys Ile Asn Lys Ser Leu
                185                 190

aaccttgctt ataagtttta cgctatgttg ctcgaattct ttaaacttgt tctaaagata   3561

ttatatattt gaaggaggtg tcacaaatgc atcacatttt tagagattcc gaccaatatt   3621

agttttatgt aatctaattt tcagagcatc tttgccttgt actgatcatt gttacccttt   3681

ttttcttcat gcag cca tgc agg gat gca cca acg gtacgttaat tgcatttgat   3736
                Pro Cys Arg Asp Ala Pro Thr
                        195

ttgataaaaa aaaaaagcct aaaatatatt tgaattttaa ttgaaaggtt ataataattc   3796

ttaactttgg gcaggaccta ttaccccttg cactatttaa tagtgtattt taaagatata   3856

aaagtgttta gttgaaacaa aaatttagat attcaaaaac tatttgaaaa ttactataaa   3916

ttgcaatttt tttgcatatc aatatgatta aaaaatatta gttaaagttc ttatgatttg   3976

attctaaaaa taaaaatcat gacaaacaat agtagacgga gaaagtatat aacaatacct   4036

cttcaagtag aatcgatttg tacacacacc tcaaaaccta cgttttcttc gatttatatt   4096

tcctatttct tttaatagta atcaaaggct attagttctg tcaaaatcta tacattggaa   4156

actctatctt tgacgcctcg tacattcgag atcgttgaac aatggatgaa tgattattta   4216

actttgtatt taaatattaa aactaatatt gtttaatttt cag gcc tta acc ttc     4271
                                                Ala Leu Thr Phe
                                                200

tgg aat tgc aaa aat ttg aaa gtg aat aat cta aag agt aaa aat gca     4319
Trp Asn Cys Lys Asn Leu Lys Val Asn Asn Leu Lys Ser Lys Asn Ala
    205                 210                 215

caa caa att cat atc aaa ttt gag tca tgc act aat gtt gta gct tca     4367
Gln Gln Ile His Ile Lys Phe Glu Ser Cys Thr Asn Val Val Ala Ser
220                 225                 230                 235

aat ttg atg atc aat gct tca gca aag agc cca aat act gat gga gtc     4415
Asn Leu Met Ile Asn Ala Ser Ala Lys Ser Pro Asn Thr Asp Gly Val
                240                 245                 250

caa gta tca aat act caa tat att caa ata tct gat act att att gga     4463
Gln Val Ser Asn Thr Gln Tyr Ile Gln Ile Ser Asp Thr Ile Ile Gly
            255                 260                 265
```

-continued

```
aca g gtttatttat ttaattttta tttatccaat ttaattagaa aaaaaaagga       4517
Thr

gtatttttat ttgataacta aattattaat ttttaatttt tttttatag gt  gat gat  4574
                                                    Gly Asp Asp
                                                        270

tgt att tca att gtt tct gga tct caa aat gtg cag gcc aca aat att   4622
Cys Ile Ser Ile Val Ser Gly Ser Gln Asn Val Gln Ala Thr Asn Ile
            275                 280                 285

act tgt ggt cca ggt cat ggt ata ag  gtactctatt ttacaaatat         4668
Thr Cys Gly Pro Gly His Gly Ile Ser
        290                 295

acttgtttcc attttctcta tttcataaaa ggtagtatga tataataatt actttaaatc  4728

ctttaattaa tttattggca aattttttct cttgtcttta tggttaatga cttagcacaa  4788

taattagggc cgtttggatg ggcgaataaa agcagcttta aaaaagtact tttaaaagtg  4848

ttgaaactta tttttaaaat aagcagttat cggtttggat aaaagtgctg aagttgttat  4908

gtcaaacgtg aaaagggaaa aatggaagaa agaaatgtta gggttatatg ggttatttgt  4968

ataaaaatat taagcacaaa aagataaaaa tgtggtcaac ttaaaacaac ttataagcta  5028

ccctacccta ccccagcttt taacttttgg cttaaaataa gttttttttt ttaaaactta  5088

aaataagttg ttttgagtat tgccaaagag ctaaataatg caaaaaccag cttttaagtc  5148

agtttgacca gcttttaagc tgagccaaac aggctcttaa aatgtctgct tagatgtgct  5208

atatatattt gagctttttt tgaagtagta tattatcctt aagttcaaca taaaatacat  5268

gctttaacat agcacatata gttaatcaaa agacgaaatg atgaataatt ttgcgaattt  5328

gattattcac aagaaaaggg atagttcaaa gtgtacattt caatgaattg aagatatcat  5388

aaagactaaa attagaagaa tcaataattg agggatcaaa aatgttatta ccttattaaa  5448

atactattcc attttcatat taaattaact aattaagagt gttttataat ctaataaaac  5508

atgcaataat tattgacgaa atgtggtttt ggtacctata atctttctga atatttgctc  5568

tatttttttct cttttttattt ttccatggat tac t att gga agc tta gga tct   5620
                                       Ile Gly Ser Leu Gly Ser
                                                   300

gga aat tca gaa gct tat gtg tct aat gtt act gta aat gaa gcc aaa   5668
Gly Asn Ser Glu Ala Tyr Val Ser Asn Val Thr Val Asn Glu Ala Lys
        305                 310                 315

att atc ggt gcc gaa aat gga gtt agg atc aag act tgg cag           5710
Ile Ile Gly Ala Glu Asn Gly Val Arg Ile Lys Thr Trp Gln
    320                 325                 330

gtaccctccc cccccccccc ccccccacag gcccattttt ttaatttttt ttaaattttt  5770

attcgaatat caatattaaa gattaatttg atttcatgtt tgaaatttat atttggataa  5830

agtatgtatt ttactagctt tctatgttat atagaaaaaa aaatgttcag aacttcagat  5890

tattgtactc gtactaagtg taaatgtgtt gctttgttta gaagtttggt ttatccagtt  5950

ttgggtcatg attaaaccaa acttataatg aaaaggggct gcaacggccg gcccactagt  6010

gctagtatca ataggaagat ctcacgtctg tttattcaga tggacgttct tggttgaatg  6070

ttaataatta taaatttaat taacatgtaa ttaagcatta tataaattaa tgtggtttaa  6130

taatgtag gga gga tct gga caa gct agc aac atc aaa ttt ctg aat gtg  6180
         Gly Gly Ser Gly Gln Ala Ser Asn Ile Lys Phe Leu Asn Val
                 335                 340                 345

gaa atg caa gac gtt aag tat ccc ata att ata gac caa aac tat tgt   6228
Glu Met Gln Asp Val Lys Tyr Pro Ile Ile Ile Asp Gln Asn Tyr Cys
            350                 355                 360
```

-continued

```
gat cga gtt gaa cca tgt ata caa cag gtaatttttt attaacgaac         6275
Asp Arg Val Glu Pro Cys Ile Gln Gln
        365                 370

aatttattat attttattac ttcttaaatc accttacatc attaaaactt tgagattctt   6335

ttcactagtt agtaactttt tgaatagatt tttagtaaat gatattcatt attcctttta   6395

tttttcttct aatttatgga tcttttggac tatggtctaa aaatcttgtt aaagtaaact   6455

gaatatcata agaaaaaatg ttagattata atctaaattt tttataaatt attagacgtt   6515

atctaatatt ttgtatgtaa gattgagaaa catatacata aaacattaga ttcaaattta   6575

ataaatatcta aaatattgat tcaaatcaat catgactaca caaacgaata catgcagatt  6635

ctcaaacata tagatgaagt catttcaaaa cgaatcaaat atagtagagt atatccttaa   6695

aagagagcat ttgggtaaat aagtaaaaat cattaagtta taaaaaaaat tctaactcga   6755

tctctcacga ttatttaatc actttgttcc ag ttt tca gca gtt caa gtg aaa     6808
                                    Phe Ser Ala Val Gln Val Lys
                                                375

aat gtg gtg tat gag aat atc aag ggc aca agt gca aca aag gtg gcc     6856
Asn Val Val Tyr Glu Asn Ile Lys Gly Thr Ser Ala Thr Lys Val Ala
    380                 385                 390

ata aaa ttt gat tgc agc aca aac ttt cca tgt gaa gga att ata atg     6904
Ile Lys Phe Asp Cys Ser Thr Asn Phe Pro Cys Glu Gly Ile Ile Met
395                 400                 405                 410

gag aat ata aat tta gta ggg gaa agt gga aaa cca tca gag gct acg     6952
Glu Asn Ile Asn Leu Val Gly Glu Ser Gly Lys Pro Ser Glu Ala Thr
                415                 420                 425

tgc aaa aat gtc cat ttt aac aat gct gaa cat gtt aca cca cac tgc     7000
Cys Lys Asn Val His Phe Asn Asn Ala Glu His Val Thr Pro His Cys
            430                 435                 440

act tca cta gaa att tca gag gat gaa gct ctt ttg tat aat tat         7045
Thr Ser Leu Glu Ile Ser Glu Asp Glu Ala Leu Leu Tyr Asn Tyr
        445                 450                 455

taatttatac tatagatctt caatatatag cagatatgat atatcacaat aaacaaatct   7105

atatctatgt attgaataat tattattaat atgtacggat tgaagtttta ataagactac   7165

tatgtatttc tattttctag tcaaaagttt gacgattgta ctttttaatg tacaaaaata   7225

ataaaatggt tatttatatg atgtatatat ccctttggta tttcttgttg aactataatg   7285

tcattattta ataactatta tctgtgcaat gattgtattt gttaatgata cataatatat   7345

ctttcatcat tgataataag aataaaatat tttacgtcta ttactttgtg aattatatgt   7405

agattttagt ttttgtttta tttttaatta aaccgagtga aatataaaga g            7456


<210> SEQ ID NO 50
<211> LENGTH: 457
<212> TYPE: PRT
<213> ORGANISM: Lycopersicon esculentum

<400> SEQUENCE: 50

Met Val Ile Gln Arg Asn Ser Ile Leu Leu Leu Ile Ile Ile Phe Ala
1               5                   10                  15

Ser Ser Ile Ser Thr Cys Arg Ser Asn Val Ile Asp Asp Asn Leu Phe
            20                  25                  30

Lys Gln Val Tyr Asp Asn Ile Leu Glu Gln Glu Phe Ala His Asp Phe
        35                  40                  45

Gln Ala Tyr Leu Ser Tyr Leu Ser Lys Asn Ile Glu Ser Asn Asn Asn
    50                  55                  60
```

-continued

```
Ile Asp Lys Val Asp Lys Asn Gly Ile Lys Val Ile Asn Val Leu Ser
65                  70                  75                  80

Phe Gly Ala Lys Gly Asp Gly Lys Thr Tyr Asp Asn Ile Ala Phe Glu
                85                  90                  95

Gln Ala Trp Asn Glu Ala Cys Ser Ser Arg Thr Pro Val Gln Phe Val
            100                 105                 110

Val Pro Lys Asn Lys Asn Tyr Leu Leu Lys Gln Ile Thr Phe Ser Gly
        115                 120                 125

Pro Cys Arg Ser Ser Ile Ser Val Lys Ile Phe Gly Ser Leu Glu Ala
    130                 135                 140

Ser Ser Lys Ile Ser Asp Tyr Lys Asp Arg Arg Leu Trp Ile Ala Phe
145                 150                 155                 160

Asp Ser Val Gln Asn Leu Val Val Gly Gly Gly Gly Thr Ile Asn Gly
                165                 170                 175

Asn Gly Gln Val Trp Trp Pro Ser Ser Cys Lys Ile Asn Lys Ser Leu
            180                 185                 190

Pro Cys Arg Asp Ala Pro Thr Ala Leu Thr Phe Trp Asn Cys Lys Asn
        195                 200                 205

Leu Lys Val Asn Asn Leu Lys Ser Lys Asn Ala Gln Gln Ile His Ile
    210                 215                 220

Lys Phe Glu Ser Cys Thr Asn Val Val Ala Ser Asn Leu Met Ile Asn
225                 230                 235                 240

Ala Ser Ala Lys Ser Pro Asn Thr Asp Gly Val Gln Val Ser Asn Thr
                245                 250                 255

Gln Tyr Ile Gln Ile Ser Asp Thr Ile Ile Gly Thr Gly Asp Asp Cys
            260                 265                 270

Ile Ser Ile Val Ser Gly Ser Gln Asn Val Gln Ala Thr Asn Ile Thr
        275                 280                 285

Cys Gly Pro Gly His Gly Ile Ser Ile Gly Ser Leu Gly Ser Gly Asn
    290                 295                 300

Ser Glu Ala Tyr Val Ser Asn Val Thr Val Asn Glu Ala Lys Ile Ile
305                 310                 315                 320

Gly Ala Glu Asn Gly Val Arg Ile Lys Thr Trp Gln Gly Gly Ser Gly
                325                 330                 335

Gln Ala Ser Asn Ile Lys Phe Leu Asn Val Glu Met Gln Asp Val Lys
            340                 345                 350

Tyr Pro Ile Ile Ile Asp Gln Asn Tyr Cys Asp Arg Val Glu Pro Cys
        355                 360                 365

Ile Gln Gln Phe Ser Ala Val Gln Val Lys Asn Val Val Tyr Glu Asn
    370                 375                 380

Ile Lys Gly Thr Ser Ala Thr Lys Val Ala Ile Lys Phe Asp Cys Ser
385                 390                 395                 400

Thr Asn Phe Pro Cys Glu Gly Ile Ile Met Glu Asn Ile Asn Leu Val
                405                 410                 415

Gly Glu Ser Gly Lys Pro Ser Glu Ala Thr Cys Lys Asn Val His Phe
            420                 425                 430

Asn Asn Ala Glu His Val Thr Pro His Cys Thr Ser Leu Glu Ile Ser
        435                 440                 445

Glu Asp Glu Ala Leu Leu Tyr Asn Tyr
    450                 455
```